United States Patent [19]

Adams et al.

[11] Patent Number: 5,409,939
[45] Date of Patent: Apr. 25, 1995

[54] PHENYL AMIDINE THIO DERIVATIVES USEFUL AS PLATELET AGGREGATION INHIBITORS

[75] Inventors: Steven P. Adams, Andover, Mass.; Richard J. Lindmark, St. Louis, Mo.; Masateru Miyano, Salem, S.C.; Joseph G. Rico, Manchester, Mo.

[73] Assignee: G. D. Searle & Co., Chicago, Ill.

[21] Appl. No.: 17,203

[22] Filed: Feb. 12, 1993

[51] Int. Cl.$^6$ ............................................. A61K 31/44
[52] U.S. Cl. ................... 514/335; 514/539; 514/562; 546/30; 560/13; 560/17; 562/426; 562/430; 562/431
[58] Field of Search ............... 562/430, 431, 426; 546/293, 300; 560/17, 13; 514/562, 539, 335

[56] References Cited

U.S. PATENT DOCUMENTS

| | | |
|---|---|---|
| 4,517,686 | 5/1985 | Ruoslahti et al. |
| 4,578,079 | 3/1986 | Ruoslahti et al. |
| 4,589,881 | 5/1986 | Pierschbacher et al. |
| 4,614,517 | 9/1986 | Ruoslahti et al. |
| 4,661,111 | 4/1987 | Ruoslahti et al. |
| 4,683,291 | 7/1987 | Zimmerman et al. |
| 4,791,102 | 12/1988 | Bernat et al. |
| 4,792,525 | 12/1988 | Ruoslahti et al. |
| 4,857,508 | 8/1989 | Adams et al. |
| 4,879,313 | 11/1989 | Tjoeng et al. |
| 4,977,168 | 12/1990 | Bernat et al. |

FOREIGN PATENT DOCUMENTS

| | | | |
|---|---|---|---|
| 0275748 | 7/1988 | European Pat. Off. ........ | C07K 7/06 |
| 0298820 | 1/1989 | European Pat. Off. ........ | C07K 7/06 |
| 0372486 | 6/1990 | European Pat. Off. ... | C07C 279/14 |
| 0381033 | 8/1990 | European Pat. Off. ... | C07C 311/19 |
| 0410540 | 1/1991 | European Pat. Off. ........ | C07K 7/06 |
| 0445796 | 9/1991 | European Pat. Off. ........ | C07K 5/06 |
| 0478328 | 4/1992 | European Pat. Off. ... | C07C 271/22 |
| 0478362 | 4/1992 | European Pat. Off. ... | C07D 211/34 |

OTHER PUBLICATIONS

Kloczewiak, et al. *Biochem.* 23, 1767–1774 (1984).
Ruggieri, et al. *Proc. Natl. Acad. Sci.* 83, 5708–5712 (1986).
Plow, et al. *Proc. Natl. Acad. Sci.* 82, 8057–8061 (1985).
Ginsberg, et al. *J. Biol. Chem.*, 260, (7), 3931–3936 (1985).
Haverstick, et al. *Blood*, 66, (4), 946–952 (1985).
Ruoslahti and Pierschbacher *Science*, 238, 491–497 (1987).

Primary Examiner—Jose G. Dees
Assistant Examiner—Samuel Barts
Attorney, Agent, or Firm—Joy A. Serauskas; Roger A. Williams

[57] ABSTRACT

This invention relates to compounds having the following formula

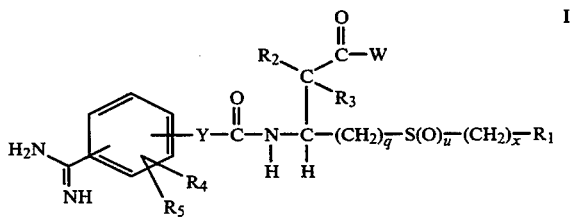

which are useful in the inhibition of platelet aggregation. This invention also relates to pharmaceutical compositions of such phenyl amidine thio derivatives.

31 Claims, No Drawings

PHENYL AMIDINE THIO DERIVATIVES USEFUL AS PLATELET AGGREGATION INHIBITORS

FIELD OF THE INVENTION

This invention is in the field of mammalian therapeutics and relates to compounds for the treatment of mammalian disorders such as cardiovascular disorders. Of particular interest is a class of phenyl amidine thio derivatives useful as inhibitors of platelet aggregation.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gp IIb/IIIa; this is an important feature of the platelet function. Inhibitors of this interaction are useful in modulating platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., Biochem. 23, 1767–1774 (1984); Plow et al., Proc. Natl. Acad. Sci. 82, 8057–8061 (1985); Ruggeri et al., Ibid. 83, 5708–5712 (1986); Ginsberg et al., J. Biol. Chem. 260 (7), 3931–3936 (1985); Haverstick et al., Blood 66 (4), 946–952 (1985); and Ruoslahti and Pierschbacher, Science 238, 491–497 (1987). Still other such inhibitory peptides are disclosed in EP Patent Applications 275,748 and 298,820.

U.S. Pat. No. 4,879,313 discloses compounds useful as inhibitors of platelet aggregation having the formula:

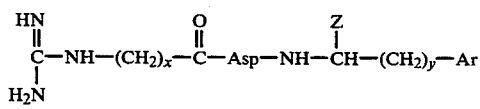

wherein
x=6 to 10,
y=0 to 4,
Z=H, COOH, CONH$_2$ OR C$_{1-6}$ alkyl,
Ar=phenyl, biphenyl or naphthyl, each substituted with 1 to 3 methoxy groups, or an unsubstituted phenyl, biphenyl, naphthyl, pyridyl or thienyl group, and
Asp=aspartic acid residue. These compounds lack the phenyl amidine moiety and the sulfonyl moiety of the present invention.

U.S. Pat. No. 4,977,168 discloses compounds having the following structural formula:

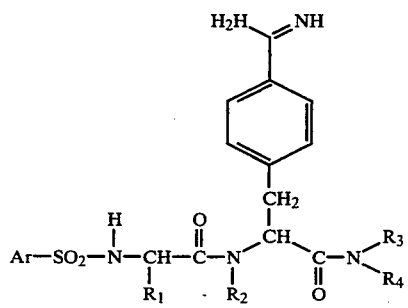

wherein
R$_1$ represents hydrogen, a lower alkyl group, a lower hydroxyalkyl group, a benzyl group, a phenyl group or a 4-hydroxyphenyl group;

R$_2$ represents a lower alkyl, lower alkenyl, lower alkynyl or benzyl group, or a lower alkoxycarbonylalkyl, lower carboxyalkyl, or lower hydroxyalkyl group;

R$_3$ and R$_4$, identical or different, each represents a lower alkyl or lower hydroxyalkyl radical, lower alkenyl or lower alkynyl radical or form together with the nitrogen to which they are attached, a saturated heterocycle such as morpholino, thiomorpholino, pyrrolidino nor substituted or substituted by an alkoxycarbonyl or carboxy group, piperazino, 4-(lower alkyl)piperazino, 4-(lower hydroxyalkyl)piperazine, or piperidino nor substituted or substituted by one of the following groups: lower alkyl, benzyl, hydroxy, lower hydroxyalkyl, amino, lower aminoalkyl, hydroxyamino, alkoxycarbonyl or carboxy.

Ar represents a phenyl, alpha-naphthyl or beta-naphthyl group, possibly substituted, or a heteroaryl group chosen from the radicals pyridyl, quinolinyl, or isoquinolinyl, possibly substituted, as well as their isomers and their mixtures and their salts with pharmaceutically acceptable mineral or organic acids which are useful as antithrombotic agents.

These compounds are structurally distinct from the present invention because they are amidinophenylalaninamides.

U.S. Pat. No. 4,791,102 discloses compounds having the following structural formula

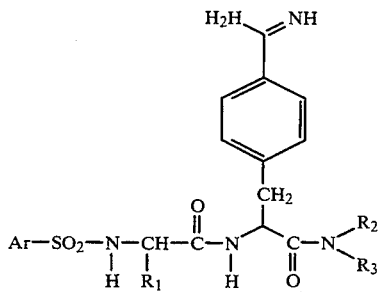

wherein
- $R_1$ represents a lower alkyl, lower hydroxyalkyl, or benzyl group, a phenyl or a 4-hydroxyphenyl group.
- $R_2$ and $R_3$, identical or different, each represents a lower alkyl or hydroxyalkyl, lower alkenyl or lower alkynyl radical, or they form together with the nitrogen to which they are attached, a saturated heterocycle such as morpholino, thiomorpholino, pyrrolidino unsubstituted or substituted by an alkoxycarbonyl or carboxyl group, piperazino, 4-(lower alkyl)-piperazino or piperidino unsubstituted or substituted by a lower alkyl, benzyl, hydroxy, lower hydroxyalkyl, amino, lower aminoalkyl, alkoxycarbonyl or carboxyl group.
- Ar represents a phenyl, a possibly substituted alpha-naphthyl or beta-naphthyl group, or else a heteroaryl group chosen from pyridyl, quinolinyl, isoquinolinyl, possibly substituted which are useful as selective inhibiting agents of thrombin and antithrombotics.

These compounds are structurally distinct from the present invention because they are amidino-phenylalaninamides.

European Patent Application 372,486 discloses N-acyl beta amino acid derivatives of the formula:

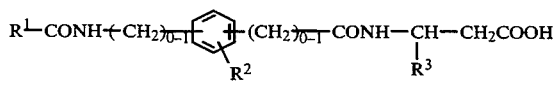

and their salts. Said compounds are useful for inhibiting platelet aggregation in the treatment of thrombosis, stroke, myocardial infarction, inflammation and arteriosclerosis, and for inhibiting metastasis.

European Patent Application 381,033 A1 discloses amidino or guanidino-aryl substituted alkanoic acid derivatives which are useful for the treatment of thrombosis, apoplexy, cardiac infarction, inflammation, arteriosclerosis and tumors. These compounds are structurally distinct from the present invention because they lack the sulfur moiety of the present invention.

European Patent Application 445,796 A2 discloses acetic acid derivatives having the formula

where
- $Q^1$ stands for hydrogen, methyl or phenyl,
- $Q^2$ stands for hydrogen, phenyl-low-alkyl or low alkyl that can be cleaved under physiological conditions,
- X stands for 1,4-phenylene, 2,5- or 3,6-pyridylene or, 1,4-piperidinylene, which is bonded to group Y through the C atom in the 4-position,
- Y is a group having the formula

 (Y¹)

 (Y²)

 (Y³)

 (Y⁴)

 (Y⁵)

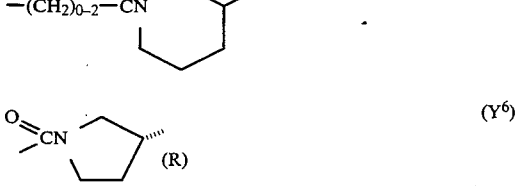 (Y⁶)

or

 (Y⁷)

where
- $Q^3$ stands for hydrogen, methyl, phenyl, —COOH, —COO—low-alkyl, —CONH(CH₂)₂—COOH or —CONH(CH₂)₂—COO—low-alkyl,
- $Q^4$ hydrogen, methyl or phenyl,
- Z a 1,4-piperazinylene group, a 1,4-piperazinylene group which is bonded to the CO group through the N atom in the 1-position or a group having the formula

where
- $R^1$ stands for hydrogen, methyl, phenyl or a —COO—low-alkyl,
- $R^2$ stands for the residue of an α-aminocarboxylic acid bonded through the amino group or of an ester or amide thereof, or a group having the formula —NHCH₂CH₂—Ar, or —CO—R², or, if applicable, a mono- or di-low-alkylated carbamoyl group or a pyrrolidinoyl or piperidinoyl group,
- Ar stands for a phenyl or a phenyl substituted by low alkyl, low alkoxy, —COOH, —COO—low-alkyl, —O(CH₂)₁₋₄—COOH, —O(CH₂)₁₋₄—COO—low-alkyl, —CONH₂, —CONH—low-alkyl, —CON(-low alkyl)₂, pyrrolidinoyl or piperidinoyl which are said to have inhibitory action on the bonding of adhesive proteins to blood platelets as well as blood platelet aggregation and cell-cell adhesion.

These compounds are structurally distinct from the present invention because the lack the sulfur moiety of the present invention.

SUMMARY OF THE INVENTION

The present invention relates to a class of compounds represented by the formula:

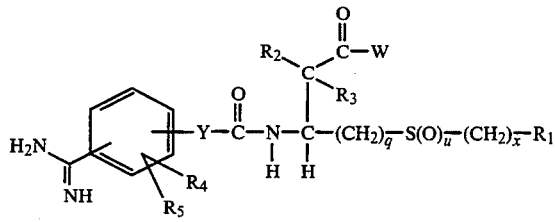

or a pharmaceutically acceptable salt thereof, wherein R₁ is alkyl having 1 to 6 carbon atoms; phenyl; substituted phenyl wherein each substituent can be selected from the group consisting of alkyl having 1 to 6 carbon atoms, halo, alkoxy having 1 to 6 carbon atoms, carboxyl, trifluoromethyl, hydroxy and nitro; or a hetero aromatic ring having 5 or 6 ring carbon atoms wherein one of the ring carbon atoms is replaced by a hetero atom selected from nitrogen, oxygen and sulfur;

R₂ and R₃ are each independently hydrido or alkyl having 1 to 6 carbon atoms;

R₄ and R₅ are each independently hydrido, alkyl having 1 to 6 carbon atoms, alkoxy having 1 to 6 carbon atoms or halo;

Y is alkyl having 1 to 6 carbon atoms, alkenyl having 2 to 4 carbon atoms or alkynyl having 2 to 4 carbon atoms;

W is OR wherein R is hydrido or alkyl having 1 to 6 carbon atoms;

q is an integer from 1 to 4;

u is 0, 1, or 2; and x is an integer from 0 to 3.

The invention further relates to pharmaceutical compositions comprising a compound of Formula I. Such compounds and compositions have usefulness as inhibitors of platelet aggregation. The invention also relates to a method of inhibiting platelet aggregation in a mammal in need of such treatment.

A preferred embodiment of the present invention is a compound of the formula

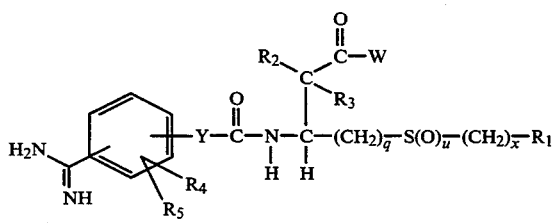

or a pharmaceutically acceptable salt thereof, wherein

R₁ is alkyl having 1 to 6 carbon atoms, phenyl, substituted phenyl wherein each substituent can be selected from the group consisting of alkyl having 1 to 6 carbon atoms, halo, alkoxy having 1 to 6 carbon atoms, carboxyl, trifluoromethyl, hydroxy and nitro; or a hetero aromatic ring having 5 or 6 ring carbon atoms wherein one of the ring carbon atoms is replaced by a hetero atom selected from nitrogen, oxygen and sulfur;

R₂ and R₃ are each independently hydrido or alkyl having 1 to 6 carbon atoms;

R₄ and R₅ are each independently hydrido, alkyl having 1 to 6 carbon atoms, alkoxy having 1 to 6 carbon atoms or halo;

Y is alkyl having 1 to 6 carbon atoms, alkenyl having 2 to 4 carbon atoms or alkynyl having 2 to 4 carbon atoms;

W is OR wherein R is hydrido or alkyl having 1 to 6 carbon atoms;

q is an integer from 1 to 4;

u is 2; and x is an integer from 0 to 3.

Exemplifying this embodiment are the following compounds:

(±)-3-[[5-[4-(aminoiminomethyl)phenyl]-1-oxopentyl]amino]-5-[(phenylmethyl)sulfonyl]pentanoic acid;

(±)-3-[[5-[4-(aminoiminomethyl)phenyl]-1-oxopentyl]amino]-4-[(4-methylphenyl)sulfonyl]butanoic acid;

(±)-3-[[5-[4-(aminoiminomethyl)phenyl]-1-oxopentyl]amino]-4-(2-pyridinylsulfonyl)butanoic acid;

(±)-ethyl 3-[[5-[4-(aminoiminomethyl)phenyl]-1-oxopentyl]amino]-4-[(4-methylphenyl)sulfonyl]butanoate;

(±)-3-[[5-[4-(aminoiminomethyl)phenyl]-1-oxopentyl]amino]-4-(phenylsulfonyl)butanoic acid;

(±)ethyl 3-[[5-[4-(aminoiminomethyl)phenyl]-1-oxopentyl]amino]-4-(phenylsulfonyl)butanoate;

(±)-3-[[5-[4-(aminoiminomethyl)phenyl]-1-oxopentyl]amino]-5-(methylsulfonyl)pentanoic acid;

(±)-3-[[5-[4-(aminoiminomethyl)phenyl]-1-oxopentyl]amino]-4-[(4-methoxyphenyl)sulfonyl]butanoic acid;

(±)-ethyl 3-[[5-[4-(aminoiminomethyl)phenyl]-1-oxopentyl]amino]-4-(2-pyridinylsulfonyl)butanoate;

(±)-3-[[5-[4-(aminoiminomethyl)phenyl]-1-oxopentyl]amino]-4-(4-fluorophenyl)sulfonyl]butanoic acid;

4-(aminoiminomethyl)-N-[2-[(4-methylphenyl)sulfonyl]ethylbenzenepentanamide;

(±)-3-[[5-[4-(aminoiminomethyl)phenyl]-1-oxopentyl]amino]-4-[(4-methoxyphenyl)sulfonyl]butanoic acid;

ethyl 3S-[[5-[4-(aminoiminomethyl)phenyl]-1-oxopentyl]amino]-4-(2-pyridinylsulfonyl)butanoate; and 1-methylethyl 3S-[[5-[4-(aminoiminomethyl)phenyl]-1-oxopentyl]amino]-4-(2-pyridinylsulfonyl)butanoate.

A further preferred embodiment of the present invention is a compound of the formula

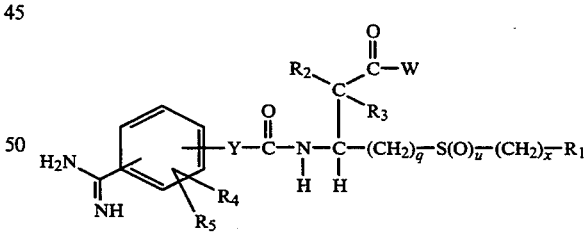

or a pharmaceutically acceptable salt thereof wherein

R₁ is alkyl having 1 to 6 carbon atoms, phenyl, or substituted phenyl wherein each substituent can be selected from the group consisting of alkyl having 1 to 6 carbon atoms, halo, alkoxy having 1 to 6 carbon atoms, carboxyl, trifluoromethyl, hydroxy and nitro;

R₂ and R₃ are each independently hydrido or alkyl having 1 to 6 carbon atoms;

R₄ and R₅ are each independently hydrido, alkyl having 1 to 6 carbon atoms, alkoxy having 1 to 6 carbon atoms or halo;

Y is alkyl having 1 to 6 carbon atoms, alkenyl having 2 to 4 carbon atoms or alkynyl having 2 to 4 carbon atoms;

W is OR wherein R is hydrido or alkyl having 1 to 6 carbon atoms;
q is an integer from 1 to 4;
u is 1; and
x is an integer from 0 to 3.

Exemplifying this embodiment are the following compounds:

(±)-3-[[5-[4-(aminoiminomethyl)phenyl]-1-oxopentyl]amino]-4-[(phenylsulfinyl)]butanoic acid;
(±)-ethyl 3-[[5-[4-(aminoiminomethyl)phenyl]-1-oxopentyl]amino]-4-(4-phenylsulfinyl]butanoate;
(±)-3-[[5-[4-(aminoiminomethyl)phenyl]-1-oxopentyl]amino]-5-(methylsulfinyl)pentanoic acid;
4-(aminoiminomethyl)-N-[2-[(4-methylphenyl)sulfinyl]ethyl]benzenepentanamide;
(±)-ethyl 3-[[5-[4-(aminoiminomethyl)phenyl]-1-oxopentyl]amino]-5-[(phenylmethyl)sulfinyl]pentanoate; and
(±)-3-[[5-[4-(aminoiminomethyl)phenyl]-1oxopentyl]amino]-5-[(phenylmethyl)sulfinyl]pentanoic acid.

Another preferred embodiment of the present invention is a compound of the formula

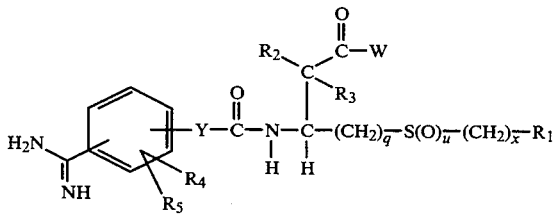

or a pharmaceutically acceptable salt thereof wherein
$R_1$ is alkyl having 1 to 6 carbon atoms, phenyl, or substituted phenyl wherein each substituent can be selected from the group consisting of alkyl having 1 to 6 carbon atoms, halo, alkoxy having 1 to 6 carbon atoms, carboxyl, trifluoromethyl, hydroxy and nitro;
$R_2$ and $R_3$ are each independently hydrido or alkyl having 1 to 6 carbon atoms;
$R_4$ and $R_5$ are each independently hydrido, alkyl having 1 to 6 carbon atoms, alkoxy having 1 to 6 carbon atoms or halo;
Y is alkyl having 1 to 6 carbon atoms, alkenyl having 2 to 4 carbon atoms or alkynyl having 2 to 4 carbon atoms;
W is OR wherein R is hydrido or alkyl having 1 to 6 carbon atoms;
q is an integer from 1 to 4;
u is 0; and
x is an integer from 0 to 3.

Exemplifying this embodiment are the following compounds:

(±)-3-[[5-[4-(aminoiminomethyl)phenyl]-1-oxopentyl]amino]-5-(methylthio)pentanoic acid;
(±)-3-[[5-[4-(aminoiminomethyl)phenyl]-1-oxopentyl]amino]-4-[(4-fluorophenyl)thio]butanoic acid;
(±)-3-[[5-[4-(aminoiminomethyl)phenyl]-1-oxopentyl]amino]-4-(phenylthio)butanoic acid;
(±)-ethyl 3-[[5-[4-(aminoiminomethyl)phenyl]-1-oxopentyl]amino]-4-[(4-phenylthio)]butanoate.

As used herein, the term "hydrido" denotes a single hydrogen atom (H). This hydrido group may be attached, for example, to a oxygen atom to form a hydroxyl group; or, as another example, two hydrido groups may be attached to a carbon atom to form a —CH$_2$—group.

As used herein, the term "alkyl" embraces a linear or branched chain saturated hydrocarbon radical having 1 to 6 carbon atoms. Illustrative of such radicals are methyl, ethyl, propyl, 1-methylethyl, butyl, 2-methylpropyl, 1-methylpropyl, 1,1-dimethylethyl, pentyl, 3-methylbutyl, 1-methylbutyl, 1-ethylpropyl, 2,2-dimethylpropyl, 1,1-dimethylpropyl, hexyl, and 4-methylpentyl.

As used herein, the term "alkoxy" embraces linear or branched oxy-containing radicals each having alkyl portions of 1 to 6 carbon atoms. Illustrative of such groups are methoxy, ethoxy, propoxy, butoxy, 1-methylethoxy, 2-methylpropoxy, 1-methylpropoxy, 1,1-dimethylethoxy, pentenoxy, 3-methylbutoxy, 1-methylbutoxy, 1-ethylpropoxy, 2-2-dimethylpropoxy, 1,1-dimethylpropoxy, hexoxy, and 4-methylpentoxy.

As used herein the term "alkenyl" embraces linear or branched unsaturated hydrocarbon radicals having 2 to 6 carbon atoms and containing at least one carbon to carbon double bond, which carbon to carbon double bond may have either cis or trans geometry within the alkenyl moiety. Illustrative of such groups are ethenyl, propenyl, butenyl, isobutenyl, pentenyl, 3-methyl-1-butenyl, 2-methyl-2-butenyl, 2,3-dimethyl-2-butenyl, and hexenyl.

As used herein the term "alkynyl" embraces linear or branched unsaturated hydrocarbon radicals having 2 to 6 carbon atoms and containing one carbon to carbon triple bond. Illustrative of such radicals are ethynyl, propynyl, butynyl, isobutynyl, pentynyl, 2-methyl-2-butynyl, and hexynyl.

As used herein the term "halo" embraces halogen atoms. Illustrative of such atoms are chloro (Cl), fluoro (F), bromo (Br) and iodo (I).

As used herein the term "heteroaromatic" embraces an unsaturated cyclic hydrocarbon structure having 5 or 6 ring carbon atoms wherein one of the ring carbon atoms is replaced by a hetero atom selected from nitrogen, oxygen and sulfur. Illustrative of such heterocyclic hydrocarbon structures are pyridyl, furyl, and thiophenyl.

The compounds as shown in Formula I can exist in various isomeric forms and all such isomeric forms are meant to be included. Tautomeric forms are also included as well as pharmaceutically acceptable salts of such isomers and tautomers.

In the structures and formulas herein, the bond drawn across a bond of an aromatic ring can be to any available atom on the aromatic ring.

The term "pharmaceutically acceptable salt" refers to a salt prepared by contacting a compound of formula (I) with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of these salts may be prepared by conventional means by reacting, for example, the appropriate acid with the corresponding compound of Formula I.

DETAILED DESCRIPTION OF THE INVENTION

The compounds of Formula I may be prepared by standard synthetic methods combined with methods analogous to solution phase peptide synthesis [see: The Peptides: Analysis, Synthesis, Biology (E. Gross and J. Meienhofer, eds.), Vol. 1-5, Academic Press, New York)].

General synthetic sequences are outlined in the following Schemes.

In Scheme 1 is described a general synthesis of the 5-(cyanophenyl)-alkanoic, -alkenoic and -alkynoic derivatives, substituted or not. A halobenzonitrile is coupled to an omega alkenoic or alkynoic acid using a palladium based coupling reaction ["Heck Reaction-"]—*Palladium Reagents in Organic Syntheses* (Richard F. Heck), Academic Press, New York, 1985; Heck, R. F. *J. Amer. Chem. Soc.*, 1979, 12, 146-51. Tuyet, J. *J. Chem. Soc., Chem. Commun.* 1984, 1287-9]. The preferred conditions for the palladium coupling reaction generally differ for the alkynoic acid and the alkenoic acid coupling components. The preferred conditions for the alkynoic acid coupling component utilizes tetrakis(triphenylphosphine)-palladium as catalyst and piperidine as the solvent (for related conditions see: H. A. Dieck and F. R. Heck *J. Organometallic Chem.* 259-263 (1975)). Suitable conditions for the alkenoic acid coupling component utilize the phase transfer conditions of Jeffery and Larock [T. Jeffery *J. Chem. Soc. Chem. Commun.* 1287-89 (1984); R. C. Larock *Tetrahedron Lett.* 2603-2606 (1989)]. These extremely mild conditions (phase transfer agent—tetrabutylammonium salt, catalyst palladium (II) acetate, base-potassium acetate or triethylamine, dimethyl formamide)afford a good yield of coupled olefin. Compounds of Formula I where Y is a saturated chain (alkane)are obtained through a selective reduction of the double bond (Y is CH=CH) by catalytic reduction over palladium on calcium carbonate. The required omega alkenoic acids are commercially available or can be synthesized by oxidation of the omega alkenols [E. J. Corey and G. Schmidt *Tetrahedron Lett.* 399 (1979)]. The required omega alkynoic acids are commercially available or can be synthesized from omega haloalkanoic acids and lithium acetylide [W. J. DeJarlais, E. A. Emken *Synth. Commun.* 653 (1980); J. Cossy, J. P. Pete *Tetrahedron Lett.* 573 (1986)].

In Scheme 2 is described an alternative method for the preparation of the (cyanophenyl)alkenoic acid unit using a standard Wittig Reaction [B. E. Maryanoff, A. Reitz *Chem Rev.* 863-927 (1989)] with cyanobenzaldehyde and an omega substituted (carboxyalkyl)triphenylphosphonium bromide as the two reaction components [for related conditions see: *J. Am. Chem. Soc.*, 397 (1970); Ibid 6831 and 7185 (1973)].

In Scheme 3 are included examples of procedures to access compounds of Formula I where $R_4$ and $R_5$ are different from hydrogen. The substituents $R_4$ and $R_5$, (where $R_4$ and $R_5$ are each independently halo, alkyl, hydroxy, or alkoxy)can be present in the starting commercially available bromobenzonitrile (Scheme 1) cyanobenzaldehyde (Scheme 2) or introduced at a latter stage as indicated in Scheme 3. The ring can be halogenated using bromine, iodine, or chlorine (Scheme 3). Introduction of fluorine on the ring is best performed at the expense of the corresponding amino derivative, using diazotization followed by dediazonation in the presence of fluoride-containing counterion (D. E. Rosenberg and al., *Tet. Let.*, 21, 4141-4, 1980; Scheme 3a). Other modifications of this method can also be useful (Rosenfeld and Widdowson, JCS Chem. Comm. 914, 1979). An alkyl group can be introduced by low temperature lithium halogen exchange followed by quenching with the appropriate aldehyde [see: W. E. Parham, C. K. Bradsher *Acct. Chem. Res.* 300 (1982)]. The resultant alcohol can be converted to an alkyl by hydrogenolysis [*Reductions in Organic Chemistry* (M. Hudlicky, ed.), John Wiley & Sons, New York, 1984] as shown in Scheme 3. The substituents, wherein $R_4$ and $R_5$ are each independently hydroxy or alkoxy, can be introduced by low temperature lithium halogen exchange followed by quenching with the electrophilic bis(trimethylsilyl)-peroxide [(TMSO)$_2$ Scheme 3) M. Taddei and A. Ricci Synthesis 633-635 (1986)] which affords the silyl ether. The silyl ether can be converted to OH by treatment with hydrochloric acid [M. Taddei and A. Ricci ibid]. The alkoxy group (OR wherein R is alkyl having 1 to 6 carbon atoms) can be introduced by treating the derivative OH with weak base ($K_2CO_3$) and an appropriate alkyl halide [2 equivalents, see: C. F. H. Allen and J. W. Gates, Jr. *Organic Syntheses* Coll. Vol 3 140 (1955)] which will, in addition, form the ester. The ester can be selectively cleaved in the presence of the ether with one equivalent of sodium hydroxide (Scheme 3). Scheme 4a describes the conversion of the cyano group into the amidine group via the thioimidate. The thioimidate is formed by first treating the cyano compound with hydrogen sulfide ($H_2S$) followed by alkylation with methyl iodide. Next, treatment of the thioimidate with ammonium acetate affords the amidine as the salt (HI). Alternatively (Scheme 4b) the nitrile can be converted to the amidine by the use of lithium bis(trimethylsilyl)amide in an inert solvent such as diethyl ether or tetrahydrofuran (R. T. Boere et al, *J. Organomet. Chem.*, 331, 161-67, 1987).

Scheme 5 describes the general synthesis of the sulfide 5-(benzylsulfinyl)-3-aminopentanoic acid from acrolein and benzylmercaptan. In the event a solution of acrolein in dichloromethane is treated with benzylmercaptan and the resulting solution is cooled to <5° C. in an ice bath and then treated with a catalytic amount of DBU. The resulting aldehyde can be isolated by extraction of the organic solvent with water and subsequent drying of the organic layer with a salt i.e., $Na_2SO_4$. The aldehyde is treated with ethyl diazoacetate in the presence of tin chloride [E. J. Roskamp et al., *J. Org. Chem.*, 54, 5258-60 (1989)] in methylene chloride at 0° C. to give the β-keto ester. The β-keto ester is converted to the β-amino ester by reductive amination using excess ammonium formate and sodium cyanoborohydride in methanol. Saponification of the β-amino ester using base i.e., sodium hydroxide, followed by acidification and purification by crystallization or reverse phase chromatography gives 5-(benzylsulfinyl)-3-aminopentanoic.

Scheme 5a describes the general synthesis of the sulfide 4-(phenylsulfinyl)-3-aminobutanoic acid from methyl 4-chloro-3-oxobutanoate and thiophenol. In the event a solution of methyl 4-chloro-3-oxobutanoate in DMF is treated with thiophenol and the resulting solution is treated with potassium carbonate and phase transfer catalyst i.e., tetrabutylammonium hydrogensulfate, at ambient temperature to give the appropriate β-keto ester. The β-keto ester is converted to the β-amino ester by reductive amination using excess ammonium formate and sodium cyanoborohydride in methanol. Saponification of the β-amino ester using base i.e., lithium hydroxide, followed by acidification and purification by crystallization or reverse phase chromatography gives 4-(phenylsulfinyl)-3-aminobutanoic acid.

Scheme 6 outlines an alternate general route for the preparation of optically active benzyl 4-(2-pyridylsulfinyl)-3 aminobutanoate. The appropriately protected β-benzyl-N-t-BOC-L-aspartic acid is converted to the optically active alcohol using diborane in THF at 0° C. [C. Stanfield et al., *J. Org. Chem.*, 6, 4797-8 (1981)]. The protected amino alcohol is treated with methylsulfonyl chloride in methylene chloride with triethylamine at 0° C. to give the desired product after appropriate extraction. The mesylated amino alcohol is then treated, in a mixture of phase transfer catalyst in DMF with a catalytic amount of DMAP present, with the appropriate mercaptan to give the BOC β-amino ester sulfide. The mixture is then treated with HCl to remove the BOC protecting group from the amine. The β-amino ester sulfide is purified by reverse phase chromatography.

Compounds of Formula I can be obtained by coupling any one of the acid derivatives obtained in Schemes 1-4 with any of the amines obtained as described in Schemes 5-6. As outlined in Scheme 7, coupling is effected with an activated form of the acid which may include anhydride, acid chloride or any of a variety of active esters as described in *Principles of Peptide Synthesis*, Bodansky, 1984, Springer-Verlag. Preferentially, the amide bonds are formed using standard coupling reagents, e.g. dicyclohexylcarbodiimide (DCC), carbonyldiimidazole, disuccinimidyl carbonate (DSC), benzotriazole-1-yl-oxy-tris-(dimethylamino)-phosphonium hexafluorophosphate (BOP) or isobutyl chloroformate (mixed anhydride method).

Scheme 7 also shows a method by which to obtain the corresponding sulfoxides and sulfones utilizing acetic acid and hydrogen peroxide under aqueous conditions and purification by reverse phase chromatography. The ethyl esters of the appropriate sulfides, sulfoxides and sulfones are prepared by treatment of the corresponding sulfides, sulfoxides and sulfones in ethanol and 4N HCl in dioxane for a period of time.

Purification of final compounds is usually by reverse phase high performance liquid chromatography [*High Performance Liquid Chromatography Protein and Peptide Chemistry*, F. Lortspeich, A. Henscher, K. P. Hupe, eds.) Walter DeGruyter, New York, 1981) or crystallization.

SCHEME 1

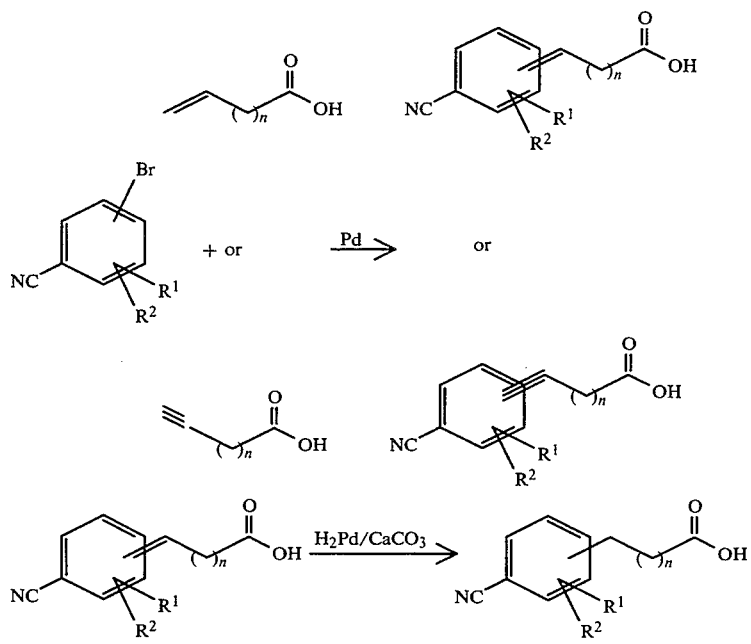

n is an integer from 1 to 3
m is an integer from 0 to 5

SCHEME 2

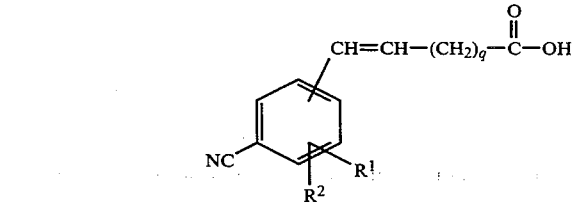

q is an integer from 1 to 4
PPhhd 3 is triphenylphosphorane

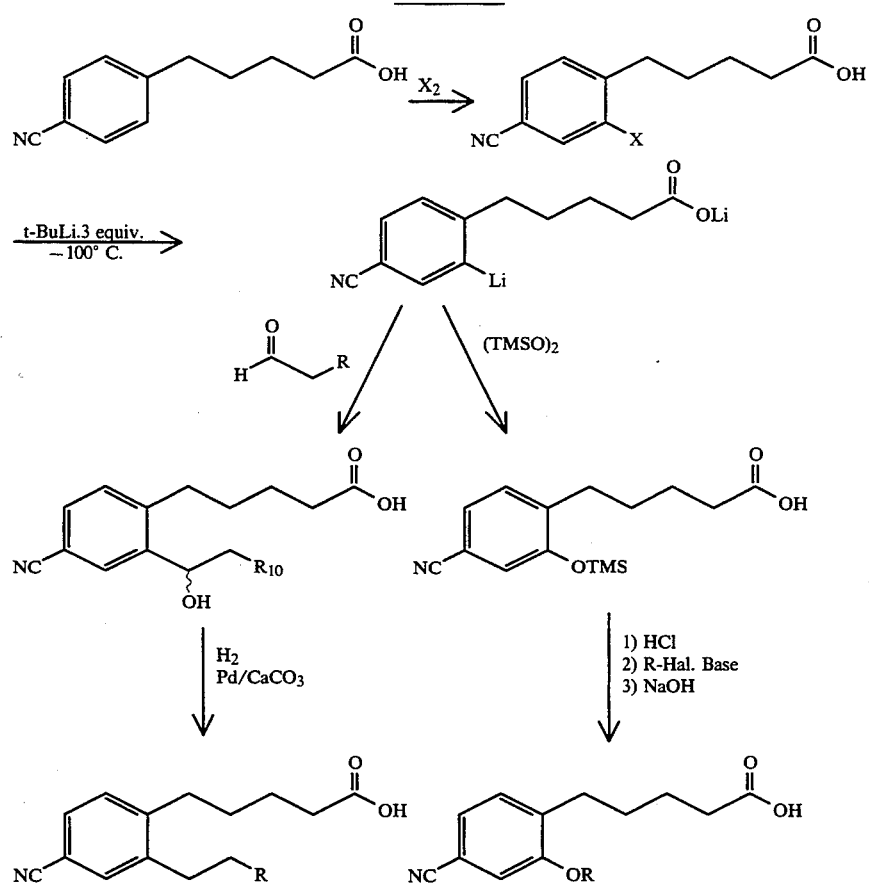
In the above scheme R is alkyl having 1 to 4 carbon atoms.
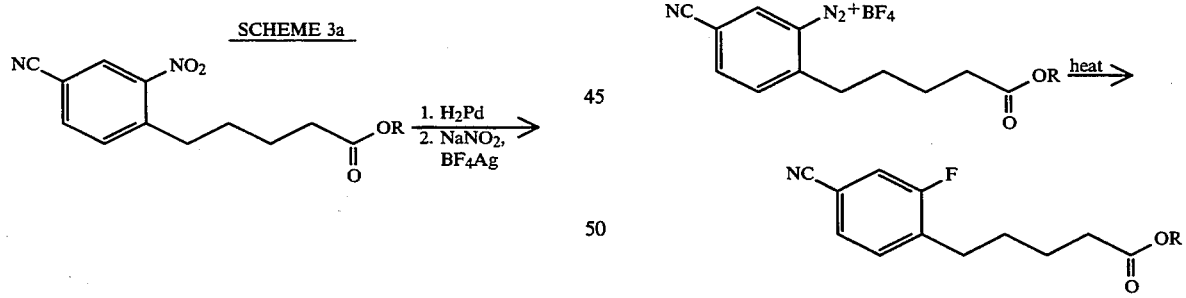
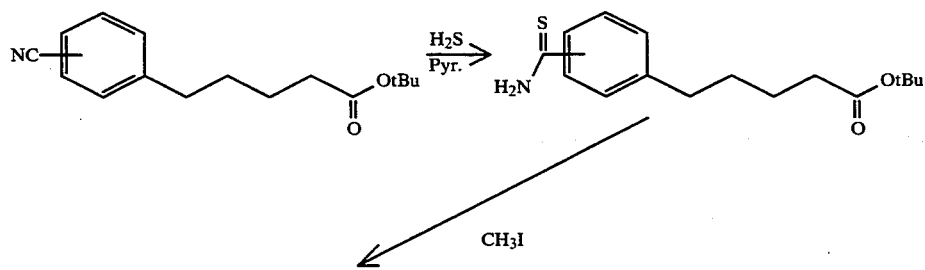

-continued
SCHEME 4a
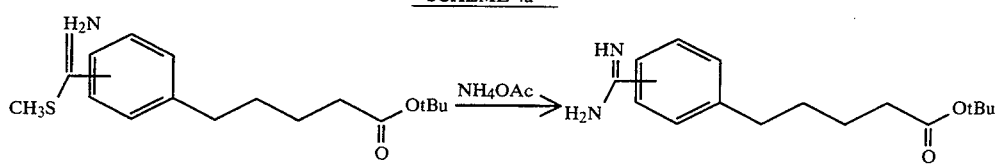
SCHEME 4b
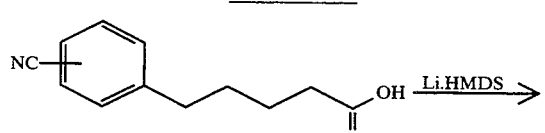
SCHEME 5a
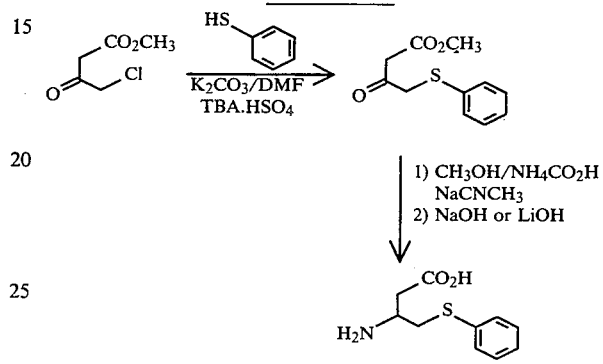
SCHEME 5
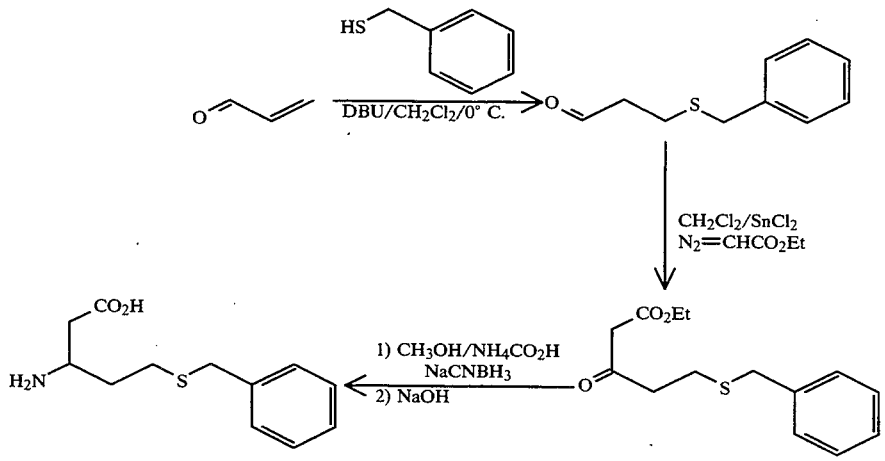
DBU = 1,8-Diazabicyclo[5.4.0]undec-7-ene
The mercaptan that is used is not limited to aryl mercaptans
TBA.HSO₄ = Tetrabutylammonium hydrogen sulfate
The mercaptan that is used is not limited to aryl mercaptans
SCHEME 6
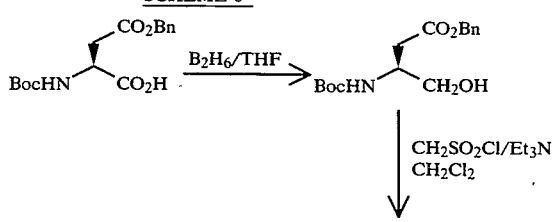

SCHEME 6
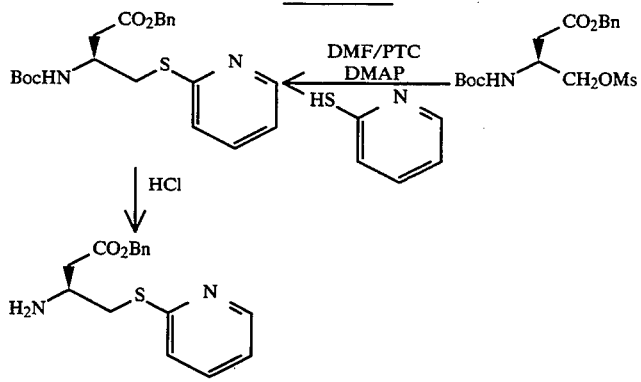
DMAP = 4-(N,N-Dimethylamino)pyridine
THF = Tetrahydrofuran
DMF = N,N-Dimethylforamide
PTC = Phase Transfer Catalyst ie., 18-Crown-6
The mercaptans utilized are not limited to aryl mercaptans

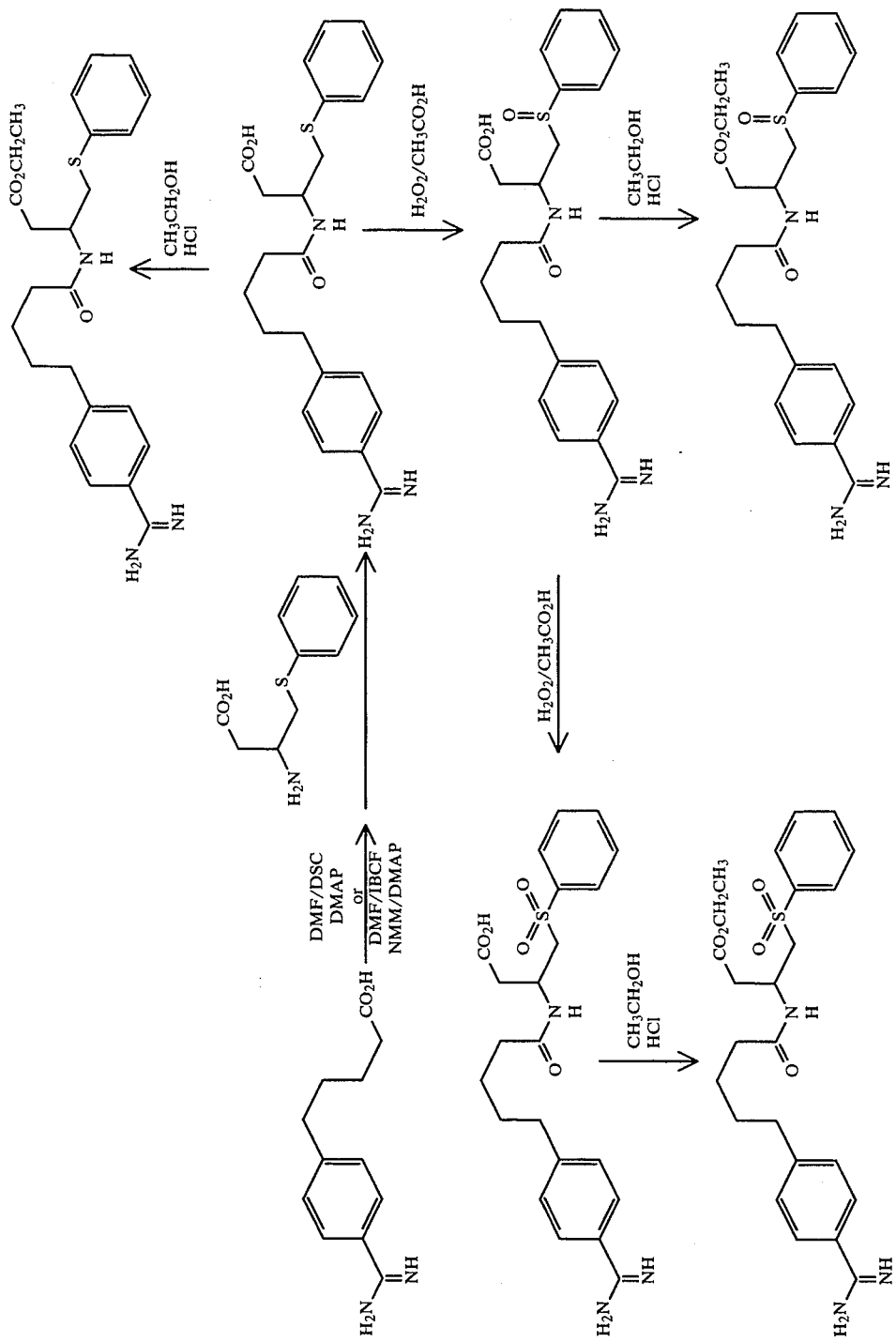
SCHEME 7
DMAP = 4-Dimethylaminopyridine
NMM = 4-Methylmorpholine
DMF = N,N-Dimethylforamide
PTC = Phase Transfer Catalyst ie., 18-Crown-6
IBCF = Isobutylchloroformate
DSC = N,N'-Disuccinimidyl carbonate
Compounds of Formula I can be obtained by coupling acid derivatives from Schemes 1-4 with the amines obtained in schemes 5-6

This invention also relates to a method of inhibiting platelet aggregation and more specifically, a method of treatment involving the administration of compounds of Formula I to achieve such inhibition.

For the inhibition of platelet aggregation, compounds of Formula I may be administered orally, parenterally, or by inhalation spray or rectally in dosage unit formulations containing conventional non-toxic pharmaceutically acceptable carriers, adjuvants and vehicles. The term parenteral as used herein includes, for example, subcutaneous, intravenous, intramuscular, intrasternal, infusion techniques or intraperitoneally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus dosage regimen may vary widely. Dosage levels of the order from about 0.01 mg to about 150 mg per kilogram of body weight per day are useful in the treatment of the above-indicated conditions (from about 10 mg to about 1.5 g per patient per day). For oral administration a daily dose of from about 0.01 to 150 mg/Kg body weight, particularly from about 1 to 30 mg/Kg body weight may be appropriate. For administration by injection a preferred daily dose would be from about 0.01 to 50 mg/Kg body weight.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may contain, for example, an amount of active ingredient from about 1 to 250 mg, preferably from about 25 to 150 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 50 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The following Examples are intended to further illustrate the present invention and not to limit the invention in spirit or scope. In the Examples, all parts are parts by weight or volume and temperature is in degrees Celsius unless otherwise expressly set forth.

EXAMPLE 1

Preparation of (±)-3-[[5-[4-(aminoiminomethyl)phenyl]-1-oxopentyl]amino]-5-[(phenylmethyl)sulfinyl]pentanoic acid.

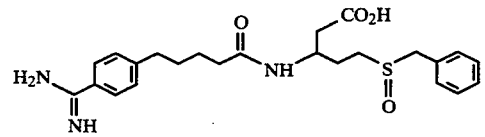

Step 1. Preparation of (±)-3-amino-5-(benzylthio)pentanoic acid:

To acrolein (5 ml) in methylene chloride (125 ml) stirring at 0° C. was added 1,8-diazabicyclo[5.4.0]undec-7-ene (DBU) (100 mg) and benzyl mercaptan (8.2 ml). After completion of the Michael addition as determined by TLC, (30% ethylacetate in hexanes), ethyl diazoacetate (7.88 ml) was added followed by tin(II)-chloride (250 mg) and the reaction was left to stir until TLC showed a single product. The reaction mixture was diluted with 100 ml methylene chloride, washed with 50 ml 10% aq. HCl, dried over $Na_2SO_4$ and solvent was removed under reduced pressure to give the β-ketoester. $^1H$ NMR($d_6$-DMSO) δ1.3 (t, 3H, J=7.8 Hz), 2.7 (m, 2H), 2.8 (m, 2H), 3.4 (s, 2H), 3.7 (s, 2H), 4.2 (q, 2H, J=7.8 Hz). The crude β-keto ester (10 g, 57 mmol) was dissolved in methanol (225 ml) and ammonium formate (36 g, 570 mmol) and $NaCNBH_3$ (3.7 g, 57 mmol) were added. The reaction was stirred at room temperature for 24 h and the solvent was removed under reduced pressure to afford a white mass which was taken up in 200 ml methylene chloride and filtered. Solvent was removed under reduced pressure to afford an oil which was dissolved in 1N HCl (200 ml) and extracted with ether (2×50 ml). The ether layers were discarded and the aqueous layer was adjusted to pH 10 with aqueous sodium hydroxide 50% solution. After 1 hr. the reaction was acidified with trifluoroacetic acid. The product was purified by reverse phase HPLC (water/acetonitrile) providing 3.5 g of a white solid [3-amino-5-(benzylsulfide)pentanoic acid]: $^1H$ NMR ($d_6$-DMSO) δ1.96 (m, 2H), 2.55 (m, 2H), 2.69 (m, 2H), 3.52 (m, 1H), 3.75 (s, 2H), 7.4 (m, 5H), 8.3 (bs, 2H); MS (FAB) m/e 240.0 (M+H+).

Step 2. Coupling of 5-(p-benzamidine)pentanoic acid (BAP) with (±)-3-amino-5-(benzylsulfide)pentanoic acid from step 1.

5-(p-Benzamidine)pentanoic acid (1.5 g.) [The required omega alkynoic acids are commercially available or can be synthesized from omega haloalkanoic acids and lithium acetylide [W. J. DeJarlais, E. A. Emken *Synth. Commun.* 653 (1980); J. Cossy, J. P. Pete *Tetrahedron Lett.* 573 (1986)]] was added to dry DMF (20 ml) under a nitrogen atmosphere and N,N'-disuccinimidyl carbonate (1.5 g) and DMAP (100 mg) were added. After the reaction became homogeneous the β-amino acid from step 1 (2 g) in aqueous 5% $K_2CO_3$ (10 ml) was added. After 1 hour, the solvent was removed under reduced pressure, the oily mass was dissolved in water (15 mL), 30% $H_2O_2$ (5 mL) and glacial acetic acid (5 ml). The oxidation was allowed to proceed for 4 h. after which the reaction mixture was worked up. The product was purified by reverse phase chromatography (water/acetonitrile) and lyophilized to give 1.6 g of the title compound as a white solid: $^1$H NMR (d$_6$-DMSO) δ1.48 (m, 2H), 1.56 (m, 2H), 1.75 (m, 2H), 2.10 (m, 2H), 2.41 (ml 2H), 2.68 (m, 2H), 3.9 (m, 1H), 4.02 (m, 2H), 7.35 (m, 9H), 7.7 (bd, 1H, J=7.9 Hz), 9.05 (bs, 2H), 9.3 (bs, 2H), MS (FAB) m/e 458.2 (M+H+).

Elemental Analysis Required for $C_{24}H_{31}N_3O_4S.F_3.C_2O_2H$ C 52.96 H 5.81 N 7.13 Found C 52.55 H 5.76 N 7.11

EXAMPLE 2

Preparation of (±)-ethyl 3-[[5-[4-aminoiminomethyl)phenyl]-1-oxopentyl]amino]-5-[(phenylmethyl)sulfinyl]pentanoate

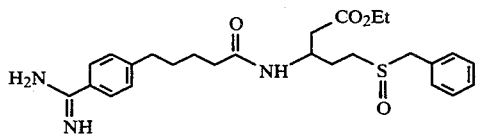

Step 1. (±)-3-[[5-[4-(Aminoiminomethyl)phenyl]-1-oxopentyl]amino]-5-[(phenylmethyl)sulfinyl]pentanoic acid (2.5 g) was added to dry ethanol (50 ml) and 4N HCl in dioxane (10 ml). This mixture was left to stir for 2 h. After complete reaction the ethanol/dioxane was removed under reduced pressure and the oily mass was dissolved in water (15 ml), acetic acid (5 ml) followed by the addition of 30% $H_2O_2$ (5 mL). The oxidation was allowed to proceed for 4 h after which the reaction mixture was worked up. The product was purified by reverse phase chromatography (water/acetonitrile) and lyophilized to give 1.69 of the title compound as a white solid: $^1$H NMR (D$_6$-DMSO) δ1.15 (t, 3H, J=7.5 Hz), 1.48 (m, 2H), 1.56 (m, 2H), 1.75 (m, 2H), 2.10 (m, 2H), 2.41 (m, 2H), 2.68 (m, 2H), 3.9 (m, 1 H), 4.0 (q, 2H, J=7.5 Hz), 4.02 (m, 2H), 7.35 (m, 9H), 7.7 (bd, 1H, J=7.9 Hz), 9.05 (bs, 2H), 9.3 (bs, 2H); MS (FAB) m/e 486.3 (M+H+).

Elemental Analysis Required for $C_{26}H_{35}N_3O_4S.F_3.C_2O_2H$ C 56.08 H 6.05 N 6.52 Found C 55.67 H 6.16 N 6.99

EXAMPLE 3

Preparation of (±)-3-[[5-[4-(aminoiminomethyl)phenyl]-1-oxopentyl]amino]-5 -[(phenylmethyl)sulfonyl]pentanoic acid

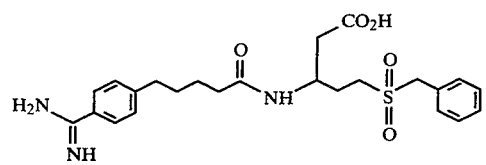

(±)-3-[[5-[4-(Aminoiminomethyl)phenyl]-1oxopentyl]amino]-5-[(phenylmethyl)sulfinyl]pentanoic acid (2.5 g) was added to water (15 ml), acetic acid (5 ml) and 30% $H_2O_2$ (10 ml). The oxidation was allowed to proceed for 24 h. after which the reaction mixture was worked up. The product was purified by reverse phase chromatography (water/acetonitrile) and lyophilized to give 1.6 g of the title compound as a white solid: $^1$H NMR (d$_6$-DMSO) δ1.48 (m, 2H), 1.56 (m, 2H), 1.75 (m, 2H), 2.10 (m, 2H), 2.41 (m, 2H), 2.68 (m, 2H), 4.05 (m, 1H), 4.22 (s, 2H), 7.35 (m, 9H), 7.7 (bd, 1H, J=7.9 Hz), 9.10 (bs, 2H), 9.8 (bs, 2H); MS (FAB) m/e 474.2 (M+H+).

Elemental Analysis Required for $C_{24}H_{31}N_3O_5S.F_3.C_2O_2H$ C 51.56 H 5.66 N 6.94 Found C 51.61 H 5.41 N 6.62

EXAMPLE 4

Preparation of (±)-3-[[5-[4-(aminoiminomethyl)phenyl]-1-oxopentyl]amino]-4 -[[(4 -methylphenyl)sulfonyl]butanoic acid

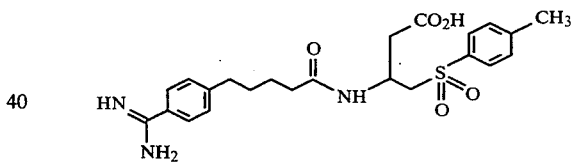

Step 1. Preparation of 3-amino-4-(4-tolylsulfide)-butanoic acid.

p-Methylthiophenol (5 g, 45 mmol) was added to $K_2CO_3$ (9.4 g, 67.5 mmol) in dry DMF (100 ml). To this mixture was added methyl 4-chloroacetoacetate (6.8 g, 45 mmol). The progress of the reaction was monitored by TLC (30% ethylacetate/hexane). After complete reaction @ 3 h, 10% aq. HCl was added and the keto-ester was extracted into ether. The solvent was removed under reduced pressure to leave 10 g of an amber oil.

The crude ketoester was dissolved in methanol (200 ml). To this solution ammonium formate (28 g, 670 mmol) was added followed by NaCNBH$_3$ (2.8 g, 67 mmol) and the solution was stirred for 24 h. The methanol was removed under reduced pressure to leave a solid mass to which was added 200 ml methylene chloride. The suspension was filtered and the filtrate concentrated under reduced pressure to leave the crude 3-amino ester. The amino ester was dissolved into 200 ml 10% aq. HCl and washed with ether (2×50 ml). The ether extracts were discarded and the aq. layer made basic (pH 10) with 50% aq. NaOH. After 1 hr. the 3-amino acid was acidified with trifluoroacetic acid and the product was isolated by reverse phase chromatography (water/acetonitrile) and lyophilized to give 3.5 g of a white solid: $^1$H NMR (d$_6$-DMSO) δ2.7 (d dd, 2H, J=7.7, 15.4, 22.2 Hz), 3.2 (d, 2H, J=2.1 Hz), 3.5 (m, 1H), 7.33 (m, 5H), 8.02 (bs, 2H).

Step 2. Coupling of 5-(p-benzamidine)pentanoic acid (BAP) with (±)3-amino-4-(p-tolylsulfide)butanoic acid in step 1.

5-(p-Benzamidine)pentanoic acid (BAP) (3.0 g, 11.3 mmol) was added to dry DMF (200 ml) followed by the addition of N-methylmorpholine (1.2 g, 11.3 mmol) and isobutyl chloroformate (1.5 g, 17 mmol) at 25° C. After the mixture was stirred for 5 min. 3-amino-4-p-tolylsulfidebutanoic acid from Step 1 (4.0 g, 11.3 mmol) was added followed by triethylamine (2.7 g,) and dimethylaminopyridine. After 1 h the solvent was removed under reduced pressure and the solid mass was dissolved in acetic acid/water (1:1) (25 ml), H$_2$O$_2$ 30% (10 ml) was added and left to stir for 2 days. After this time the solution was concentrated and the product purified by reverse phase chromatography (water/acetonitrile) to give 2.5 g of the title compound as a white solid: $^1$H NMR (d$_6$-DMSO) δ1.25 (m, 2H), 1.53 (m, 4H), 2.32(s, 3H), 2.8 (m, 2H), 2.55 (m, 2H), 2.81 (m, 2H), 3.45 (m, 2H), 4.23 (m, 1H), 7.44 (m, 5H), 7.79 (s, 4H), 7.99 (d, 1H,J=8.09 Hz), 9.05 (bs, 2H), 9.11 (bs, 2H), 10.42 (s, 1H); MS (FAB) m/e 460.1 (M+H+).

Elemental Analysis Required for C$_{23}$H$_{29}$N$_3$O$_5$S.F$_3$-C$_2$O$_2$H H$_2$O C 52.36 H 5.10 N 7.30 Found C 52.17 H 5.38 N 7.31

EXAMPLE 5

Preparation of (±)-ethyl 3-[[5-[[4-(aminoiminomethyl)phenyl]-1-oxopentyl]amino]-4-[(4-methylphenyl)sulfonyl]butanoate

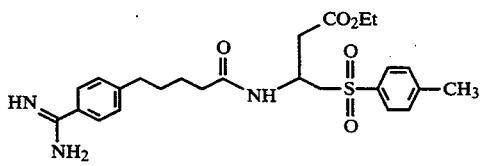

(±)-3-[[5-[4-(aminoiminomethyl)phenyl]-1-oxopentyl]amino]-4 -[[(4-methylphenyl)sulfonyl]butanoic acid (1.2 g) from example 4 was treated with dry ethanol (40 ml) and 4N HCl in dioxane (10 ml) was added. The progress of the reaction was monitored by reverse phase chromatography. After 2 hours the solvent was removed under reduced pressure, leaving a white solid which was purified by reverse phase chromatography (water/acetonitrile) and lyophilized to give 1.1 g of the title compound as a white solid: $^1$H NMR (d$_6$-DMSO) δ1.1 (t, 3H, J=7.5 Hz), 2.25 (m, 2H), 2.32 (s, 3H), 2.53 (m, 4H), 3.55 (m, 2H], 4.0 (q, 2H, J=7.5 Hz) 4.33 (m, 1H), 7.44 (m, 5H), 7.79 (s, 4H), 7.99 (d, 1H,J=8.09 Hz), 9.1 (bs, 2H), 9.19 (bs, 2H), 10.42 (s, 1H); MS (FAB) m/e 488.2 (M+H+).

Elemental Analysis Required for C$_{25}$H$_{33}$N$_3$O$_5$S.F$_3$-C$_2$O$_2$H H$_2$O C 50.90 H 5.90 N 6.59 Found C 51.03 H 5.40 N 6.40

EXAMPLE 6

Preparation of (±)-3-[[5-[4-(aminoiminomethyl)phenyl]-1-oxopentyl]amino]-4-[(4-methoxyphenyl)sulfonyl]butanoic acid

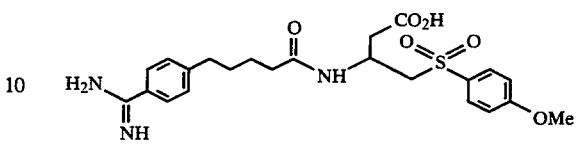

Step 1. Preparation of 3-amino-4-(p-methoxyphenylsulfide)butanoic acid.

p-Methoxythiophenol (5 g, mmol) was added to K$_2$CO$_3$ (9.4 g, 67.5 mmol) in dry DMF (100 ml). To this mixture was added methyl 4-chloroacetoacetate (6.8 g, 45 mmol). The progress of the reaction was monitored by TLC (30% ethylacetate/hexane). After complete reaction @ 3 h, 10% aq. HCl was added and the ketoester was extracted into ether to leave 10 g of an amber oil after removal of the solvent under reduced pressure.

The crude ketoester was dissolved in methanol (200 ml). To this solution ammonium formate (28 g, 670 mmol) was added followed by NaCNBH$_3$ (2.8 g, 67 mmol) and the solution was stirred for 24 h. The methanol was removed under reduced pressure to leave a solid mass, which was treated with 200 ml of methylene chloride. The suspension was filtered and the filtrate concentrated under reduced pressure to leave crude 3-amino ester. The amino ester was extracted into 200 ml 10% aq. HCl and washed with ether (2×50 ml). The ether extracts were discarded and the aq. layer made basic with 50% aq. NaOH. After 1 hr. the 3-amino acid was acidified with trifluoroacetic acid and the product was isolated by reverse phase chromatography (water/acetonitrile) to give 3.5 g of a white solid: 1H NMR (d$_6$-DMSO) δ2.7 (d dd, 2H, J=7.7, 15.4, 22.2 Hz), 3.2 (d, 2H, J=2.1 Hz), 3.5 (m, 1H), 7.33 (m, 5H), 8.02 (bs, 2H).

Step 2. Coupling of 5-(p-benzamidine)pentanoic acid (BAP) with (±)-3-amino-4-(p-methoxphenylsulfide)-butanoic acid in step 1.

5-(p-Benzamidine)pentanoic acid (BAP) (3.0 g, 11.3 mmol) was added to dry DMF (200 ml) followed by N-methylmorpholine (1.2 g, 11.3 mmol) and isobutyl chloroformate (1.5 g, 17 mmol) at 25° C. The mixture was stirred for 5 min. A solution of 3-amino-4-(p-methoxyphenylsulfide)butanoic acid (4.0 g, 11.3 mmol), 2.7 g triethylamine and dimethylaminopyridine in 20 ml dry DMF was added. After 1 h the solvent was removed under reduced pressure and the solid mass was dissolved into acetic acid:water (1:1) (25 ml) and 30% H$_2$O$_2$ (10 ml) was added. The solution was allowed to stir for 2 days. After this time the solution was purified by reverse phase chromatography (water/acetonitrile) and lyophilized to give 2.5 g of the title compound as a white solid: $^1$H NMR (d$_6$-DMSO) δ1.25 (m, 2H), 1.53 (m, 4H), 2.8 (m, 2H), 2.55 (m, 2H), 2.81 (m, 2H), 3.45 (m, 2H), 3.84 (s, 3H), 4.29 (m, 1H), 7.44 (m, 5H), 7.79 (s, 4H), 7.99 (d, 1 H,J=8.09 Hz), 9.05 (bs, 2H), 9.11 (bs, 2H), 10.42 (s, 1H); MS (FAB) m/e 476.2 (M+H+).

Elemental Analysis Required for C$_{23}$H$_{29}$N$_3$O$_6$S.F$_3$-C$_2$O$_2$H H$_2$O C 49.40 H 5.34 N 8.98 Found C 49.74 H 5.07 N 7.00

EXAMPLE 7

Preparation of
(±)-3-[[5-[4-(aminoiminomethyl)phenyl]-1-oxopentyl]amino]-4-[(4-fluorophenyl)thio]butanoic acid

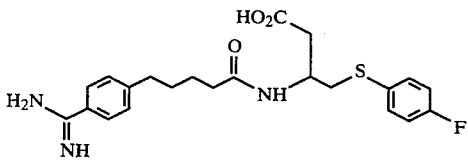

Step 1. Preparation of 3-amino-4-(p-fluorophenylsulfide)butanoic acid.

p-Fluorothiophenol (5 g, 45 mmol) was added to $K_2CO_3$ (9.4 g, 67.5 mmol) in dry DMF (100 ml). To this mixture was added methyl 4-chloroacetoacetate (6.8 g, 5 mmol). The progress of the reaction was monitored by TLC (30% ethylacetate:hexane). After complete reaction @ 3 h 10% aq. HCl was added and the ketoester was extracted into ether to leave 10 g of an amber oil after removal of the solvent under reduced pressure.

The crude β-ketoester was dissolved in methanol (200 ml). To this solution ammonium formate (28 g, 670 mmol]was added followed by $NaCNBH_3$ (2.8 g, 67 mmol) and the solution was stirred for 24 h. The methanol was removed under reduced pressure to leave a solid mass to which was added 200 ml of methylene chloride. The suspension was filtered and the filtrate concentrated under reduced pressure to leave crude the β-amino ester. The β-amino ester was dissolved into 200 ml 10% aq. HCl and washed with ether (2×50 ml). The ether extracts were discarded and the aq. layer made basic (pH 10)with 50% aq. NaOH. After 1 hr the basic solution was acidified using trifluoroacetic acid and the product was isolated by reverse phase chromatography (water/acetonitrile) and lyophilized to give 3.5 g of a white solid: $^1$H NMR ($d_6$-DMSO) δ2.7 (d dd, 2H, J=7.7, 15.4, 22.2 Hz), 3.2 (d, 2H, J=2.1 Hz), 3.5 (m, 1H), 7.33 (m, 5H), 8.02 (bs, 2H).

Step 2. Coupling of 5-(p-benzamidine)pentanoic acid (BAP) with (±)-3-amino-4-(p-fluorophenylsulfide) butanoic acid in step 1.

5-(p-Benzamidine)pentanoic acid (BAP) (3.0 g, 11.3 mmol) was added to dry DMF (200 ml) followed by DSC (1.2 g, 11.3 mmol) and DMAP (1.5 g, 17 mmol) at 25° C. The mixture was stirred for 1 hr. 3-Amino-4-(p-fluorophenylsulfide) butanoic acid (4.0 g, 11.3 mmol) was added followed by triethylamine (2.7 g,) and dimethylaminopyridine. After 24 h the solvent was removed under reduced pressure, the solid mass was treated with water and acetonitrile (50 ml, 1:1) purified by reverse phase chromatography (water/acetonitrile) and lyophilized to give 2.5 g of the title compound as a white solid: $^1$H NMR ($d_6$-DMSO) δ1.25 (m, 2H), 1.53 (m, 4H), 2.8 (m, 2H), 2.55 (m, 2H), 2.81 (m, 2H), 3.45 (m, 2H), 4.30 (m, 1H), 7.44 (m, 5H), 7.79 (s, 4H), 7.99 (d, 1 H, J=8.09 Hz), 9.05 (bs, 2H), 9.11 (bs, 2H), 10.42 (s, 1H); MS (FAB) m/e 432.2 (M+H+).

Elemental Analysis Required for $C_{22}H_{26}N_3O_3S \cdot F_3C_2O_2H \cdot H_2O$ C 51.88 H 5.09 N 7.57 Found C 51.83 H 4.92 N 7.48

EXAMPLE 8

Preparation of
(±)-3-[[5-[4-(aminoiminomethyl)phenyl]-1-oxopentyl]amino]-4-[[(4-fluorophenyl)]sulfonyl]butanoic acid

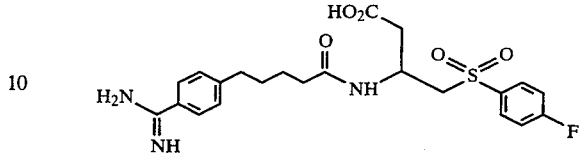

(±)-3-[[5-[4-(Aminoiminomethyl)phenyl]-1-oxopentyl]amino]-4-(4-fluorophenyl)thio]butanoic acid was dissolved in acetic acid:water (1:1) (25 ml) and 30% $H_2O_2$ was added (10 ml). The reaction mixture was then left to stir for 2 days. After this time the solution was purified by reverse phase chromatography (water/acetonitrile) and lyophilized to give 2.5g of the title compound as a white solid: $^1$H NMR ($d_6$-DMSO) δ1.25 (m, 2H), 1.53 (m, 4H), 2.8 (m, 2H), 2.55 (m, 2H), 2.81 (m, 2H), 3.45 (m, 2H), 4.29 (m, 1H), 7.44 (m, 5H), 7.79 (s, 4H), 7.99 (d, 1 H, J=8.09 Hz), 9.05 (bs, 2H), 9.11 (bs, 2H), 10.42 (s, 1H); MS (FAB) m/e 464.2 (M+H+).

Elemental Analysis Required for $C_{22}H_{26}N_3O_5S \cdot F_3C_2O_2H \cdot H_2O$ C 49.91 H 4.71 N 7.27 Found C 49.46 H 4.74 N 7.23

EXAMPLE 9

Preparation of
(±)-3-[[5-[4-(aminoiminomethyl)phenyl]-1-oxopentyl]amino]-4-(2-pyridinylsulfonyl)butanoic acid

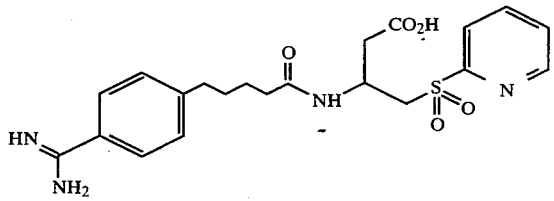

Step 1. Preparation of 3-amino-4-(2-pyridylsulfide)-butanoic acid.

2-Mercaptopyridine (5 g, 45 mmol) was added to $K_2CO_3$ (9.4 g, 67.5 mmol) in dry DMF (100 ml). To this mixture was added methyl 4-chloroacetoacetate (6.8 g, 45 mmol). The progress of the reaction was monitored by TLC (30% ethylacetate/hexane). After complete reaction @ 3 h, 10% aq. HCl was added and the ketoester was extracted into ether to leave 10 g of an amber oil after removal of the solvent under reduced pressure.

The crude ketoester was dissolved in methanol (200 ml). To this solution ammonium formate (28 g, 670 mmol) was added followed by $NaCNBH_3$ (2.8 g, 67 mmol) and the solution was stirred for 24 h. The methanol was removed under reduced pressure to leave a solid mass to which was added 200 ml methylene chloride. The suspension was filtered and the filtrate concentrated under reduced pressure to leave crude the 3-amino ester. The amino ester was extracted into 200 ml 10% aq. HCl and extract with ether (2×50 ml). The ether extracts were discarded and the aq. layer made basic with 50% aq. NaOH. After 1 h. the amino acid was acidified with trifluoroacetic acid and the product was purified by reverse phase chromatography (water- /acetonitrile) and lyophilized to give 3.5 g of a white solid: $^1$H NMR (d$_6$-DMSO) δ2.7 (d dd, 2H, J=7.7, 15.4, 22.2 Hz), 3.2 (d, H, J=2.1 Hz), 3.5 (m, 1H), 7.33 (m, 5H), 8.02 (bs, 2H).

Step 2. Coupling of 5-(p-benzamidine)pentanoic acid (BAP) with (±)-3-amino-4-(2-mercaptopyridinesulfide) butanoic acid in step 1.

5-(p-Benzamidine)pentanoic acid (BAP) (3.0 g, 11.3 mmol) was added to dry DMF (200 ml) followed by DSC (1.2 g, 11.3 mmol) and DMAP (1.5 g, 17 mmol) at 25° C. After the mixture was stirred till homogeneous, (±)-3-amino-4-(2-pyridylsulfide)butanoic acid (4.0 g, 11.3 mmol) in 10 ml of 5% K$_2$CO$_3$ was added. After 1 h. the solvent was removed under reduced pressure and the solid mass was dissolved in acetic acid/water (1:1) (25 ml) and added H$_2$O$_2$ 30% (10 ml) and left to stir for 2 days. After this time the solution was purified by reverse phase chromatography (water/acetonitrile) and lyophilized to give 2.5 g of the title compound as a white solid; $^1$H NMR (d$_6$-DMSO) δ1.25 (m, 2H), 1.53 (m, 4H), 2.8 (m, 2H), 2.55 (m, 2H), 2.81 (m 2H), 3.45 (m, 2H), 3.84 (s, 3H), 4.29 (m, 1H), 7.44 (m, 5M), 7.79 (s, 4H), 7.99 (d, 1H, J=8.09 Hz), 9.05 (bs, 2H), 9.11 (bs 2H). 10.42 (s, 1H); MS (FAB) m/e 476.2 (M+H+).

Elemental Analysis Required for C$_{23}$H$_{29}$N$_3$O$_6$S.F$_3$.C$_2$O$_2$H H$_2$O C 49.40 H 5.34 N 6.98 Found C 49.74 H 5.07 N 7.00

EXAMPLE 10

Preparation of (±)-ethyl 3-[[5-[4-(aminoiminomethyl)phenyl]-1-oxopentyl]amino-4-(2-pyridinylsulfonyl)butanoate

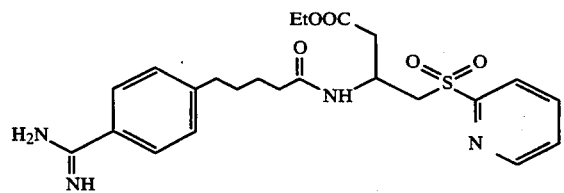

(±)-3-[[5-[4-Aminoiminomethyl)phenyl]-1-oxopentyl]amino]-4-(2-pyridinylsulfonyl)butanoic acid (1.2 g) from Example 9 was suspended in dry ethanol (40 ml) and 4N HCl in dioxane (20 ml) was added. The progress of the reaction was monitored by HPLC. After 2 hours the solvent was removed under reduced pressure leaving a white solid which was purified by reverse phase chromatography (water/acetonitrile) and lyophilized to give 1.1 g of the title compound as a white solid: $^1$H NMR (d$_6$-DMSO) δ1.1 (t, 3H, J=7.5 Hz), 2.25 (m, 2H), 2.32 (s, 3H), 2.53 (m, 4H), 3.55 (m, 2H), 4.0 (q, 2H, J=7.5 Hz) 4.33 (m, 1H), 7.44 (m, 5H), 7.79 (s, 4H), 7.99 (d, 1 H, J=8.09 Hz), 9.1 (bs, 2H), 9.19 (bs, 2H), 10.42 (s, 1H); MS (FAB) m/e 475.1 (M+H+).

Elemental Analysis Required for C$_{23}$H$_{30}$N$_4$O$_6$S.F$_3$.C$_2$O$_2$H H$_2$O C 48.34 H 4.97 N 8.68 Found C 48.00 H 4.97 N 8.66

EXAMPLE 11

Preparation of (±)-3-[[5-[4-(aminoiminomethyl)phenyl]-1-oxopentyl]amino]-4-(phenylthio)butanoic acid

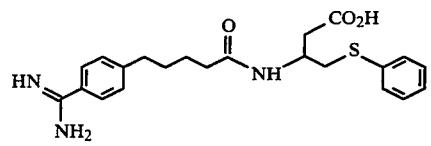

Step 1. Preparation of 3-amino-4-(phenylsulfide)-butanoic acid.

Thiophenol (5 g, 45 mmol) was added to K$_2$CO$_3$ (9.4 g, 67.5 mmol) in dry DMF (100 ml). To this mixture was added methyl 4-chloroacetoacetate (6.8 g, 45 mmol). The progress of the reaction was monitored by TLC (30% ethylacetate/hexane). After complete reaction @ 3 h, 10% aq., HCl was added and the ketoester was extracted into ether to leave 10 g of an amber oil after removal of the solvent under reduced pressure.

The crude ketoester was dissolved in methanol (200 ml). To this solution ammonium formate (28 g, 670 mmol) was added followed by NaCNBH$_3$ (2.8 g, 67 mmol) and the solution was stirred for 24 h. The methanol was removed under reduced pressure to leave a solid mass to which 200 ml of methylene chloride was added. The resulting suspension was filtered and the filtrate concentrated under reduced pressure to leave crude 3-amino ester. The amino ester was extracted into 200 ml 10% aq. HCl and then extract with ether (2×50 ml). The ether extracts were discarded and the aq. layer made basic with 50% aq. NaOH. After 1 hr. the amino acid was acidified using trifluoroacetic acid and the product was purified by reverse phase chromatography (water/acetonitrile) and lyophilized to give 3.5 g of a white solid: $^1$H NMR (d$_6$-DMSO) δ2.7 (d dd, 2H, J=7.7, 15.4, 22.2 Hz), 3.2 (d, 2H, J=2.1 Hz), 3.5 (m, 1H), 7.33 (m, 5H), 8.02 (bs, 2H).

Step 2. Coupling of 5-(p-benzamidine)pentanoic acid (BAP) with (±)-3-amino-phenylsulfidebutanoic acid in step 1.

5-(p-Benzamidine)pentanoic acid (BAP) (3.0 g, 11.3 mmol) was added to dry DMF (200 ml) followed by DSC (1.2 g, 11.3 mmol) and DMAP (1.5 g, 17 mmol) at 25° C. The mixture was stirred till homogeneous. 3-Amino-4-(thiophenylsulfide)butanoic acid (4.0 g, 11.3 mmol) in 10 ml 5% aqueous K$_2$CO$_3$ was added. After 1 h the solvent was removed under reduced pressure and the solid mass was purified by reverse phase chromatography (water/acetonitrile) and lyophilized to give 2.5 g of the title compound as a white solid. $^1$H NMR (d$_6$-DMSO) δ1.25 (m, 2H), 1.53 (m, 4H), 2.8 (m, 2H), 2.55 (m, 2H), 2.81 (m, 2H), 3.45 (m, 2H), 4.30 (m, $^1$H), 7.44 (m, 5H), 7.79 (s, 4H), 7.99 (d, 1H, J=8.09 Hz), 9.05 (bs, 2H), 9.11 (bs, 2H), 10.42 (s, 1H); MS (FAB) m/e 414.2 (M+H+).

Elemental Analysis Required for C$_{22}$H$_{27}$N$_3$O$_3$S.F$_3$.C$_2$O$_2$H H$_2$O C 52.84 H 5.54 N 7.70 Found C 53.16 H 5.05 N 7.51

EXAMPLE 12

Preparation of (±)-ethyl 3-[[5-[[4-(aminoiminomethyl)phenyl]-1-oxopentyl]amino]-4-(4-phenylthio)butanoate

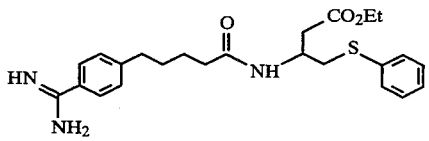

(±)-3-[[5-[4-(Aminoiminomethyl)phenyl]-1-oxopentyl]amino]-4-(phenylthio)butanoic acid (1.2 g) from Example 11 was suspended in dry ethanol (40 ml) and 4N HCl in dioxane (10 ml) was added. The progress of the reaction was monitored HPLC. After 2 h the solvent was removed under reduced pressure to leave a white solid which was purified by reverse phase chromatography (water/acetonitrile) and lyophilized to give 1.1 g of the title compound as a white solid: $^1$H NMR (d$_6$-DMSO) δ1.1 (t, 3H, J=7.5 Hz), 2.25 (m, 2H), 2.32 (s, 3H), 2.53 (m, 4H), 3.55 (m, 2H), 4.0 (q, 2H, J=7.5 Hz) 4.33 (m, $^1$H), 7.44 (m, 5H), 7.79 (s, 4H), 7.99 (d, 1H, J=8.09 Hz), 9.1 (bs, 2H), 9.19 (bs, 2H), 10.42 (s, 1H); MS (FAB) m/e 442.3 (M+H+).

Elemental Analysis Required for C$_{24}$H$_{31}$N$_3$O$_3$S.F$_3$.C$_2$O$_2$H H$_2$O C 56.21 H 5.80 N 7.56 Found C 56.05 H 5.64 N 7.40

EXAMPLE 13

Preparation of (±)-3-[[5-[4-(aminoiminomethyl)phenyl]-1-oxopentyl]amino]-4-[(phenylsulfinyl)butanoic acid

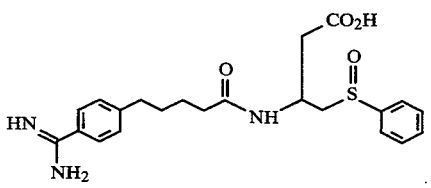

(±)-3-[[5-[4-(Aminoiminomethyl)phenyl]-1-oxopentyl]amino]-4-(phenylthio)butanoic acid (2.5 g) was added to 15 ml water and 5 ml acetic acid and 30% H$_2$O$_2$ (10 mL). The oxidation was allowed to proceed for 4 h. after which the reaction mixture was purified by reverse phase chromatography (water/acetonitrile) and lyophilized to give 1.6 g of the title compound as a white solid: $^1$H NMR (d$_6$-DMSO) δ1.48 (m, 2H), 1.56 (m, 2H), 1.75 (m, 2H), 2.10 (m, 2H), 2.41 (m, 2H), 2.68 (m, 2H), 4.05 (m. 1H), 4.22 (s, 2H), 7.35 (m, 9H), 7.7 (bd, 1H, J=7.9 Hz); 9.10 (bs, 2H), 9.8 (bs, 2H); MS (FAB) m/e 430.2 (M+H+).

Elemental Analysis Required for C$_{24}$H$_{31}$N$_3$O$_5$S.F$_3$.C$_2$O$_2$H C 51.33 H 5.38 N 7.48 Found C 51.41 H 4.85 N 7.22

EXAMPLE 14

Preparation of (±)-ethyl 3-[[5-[4-(aminoiminomethyl)phenyl]-1-oxopentyl]amino]-4-(4-phenylsulfinyl)butanoate

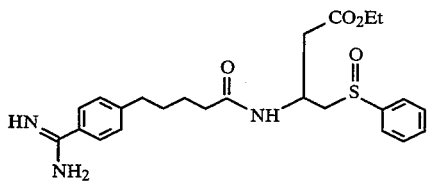

(±)-3-[[5-[4-(Aminoiminomethyl)phenyl]-1-oxopentyl]amino]-4-[(phenylsulfinyl)]butanoic acid (2.5 g) was added to dry ethanol (50 ml) and 4N HCl in dioxane (10 ml). This mixture was left to stir for 2 h. After complete reaction the solvent was removed under reduced pressure and the oily mass was purified by reverse phase chromatography (water/acetonitrile) and lyophilized to give 1.6 g of the title compound as a white solid: $^1$H NMR (d$_6$-DMSO) δ1.15 (t, 3H, J=7.5 Hz), 1.48 (m, 2H), 1.56 (m, 2H), 1.75 (m, 2H), 2.10 (m, 2H), 2.41 (m, 2H), 2.68 (m, 2H), 3.9 (m, 1H), 4.0 (q, 2H, J=7.5 Hz), 4.02 (m, 2H), 7.35 (m, 9H), 7.7 (bd, 1H, J=7.9 Hz), 9.05 (bs, 2H), 9.3 (bs, 2H) MS (FAB) m/e 458.3 (M+H+).

Elemental Analysis Required for C$_{24}$H$_{31}$N$_3$O$_4$S.F$_3$.C$_2$O$_2$H C 53.38 H 5.69 N 7.24 Found C 53.30 H 5.27 N 6.95

EXAMPLE 15

Preparation of (±)-3-[[5-[4-(aminoiminomethyl)phenyl]-1-oxopentyl]amino]-4-(phenylsulfonyl)butanoic acid

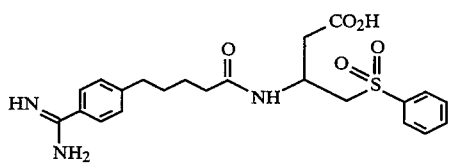

Step 1.

(±)-3-[[5-[4-(Aminoiminomethyl)phenyl]-1-oxopentyl]amino]-4-[(phenylsulfinyl)]butanoic acid (2.5 g) was dissolved in 10 ml water and 5 ml acetic acid followed by the addition of 5 ml 30% H$_2$O$_2$. The oxidation was allowed to proceed for 24 h. after which the reaction mixture was purified by reverse phase chromatography (water/acetonitrile) and lyophilized to give 1.6 g of the title compound as a white solid: $^1$H NMR (d$_6$-DMSO) δ1.48 (m, 2H), 1.56 (m, 2H), 1.75 (m, 2H), 2.10 (m, 2H), 2.41 (m, 2H), 2.68 (m, 2H), 3.9 (m, 1H), 4.02 (m, 2H), 7.35 (m, 9H), 7.7 (bd, 1H, J=7.9 Hz), 9.05 (bs, 2H), 9.3 (bs, 2H); MS (FAB) m/e 446.2 (M+H+).

Elemental Analysis Required for C$_{24}$H$_{31}$N$_3$O$_4$S.F$_3$.C$_2$O$_2$H C 50.42 H 5.11 N 7.35 Found C 50.68 H 4.84 N 7.15

EXAMPLE 16

Preparation of (±)-ethyl 3-[[5-[4-(aminoiminomethyl)phenyl]-1-oxopentyl]amino]-4-(phenylsulfonyl)butanoate

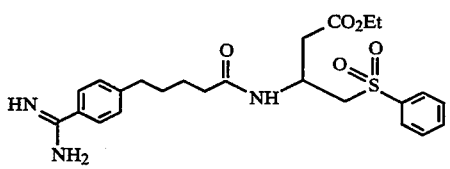

(±)-3-[[5-[4-(Aminoiminomethyl)phenyl]-1-oxopentyl]amino]-4-(phenylsulfonyl)butanoic acid (2.5 g) was added to dry ethanol (50 ml) and 4N HCl in dioxane (10 ml). This mixture was left to stir for 2 h. After complete reaction the solvent was removed under reduced pressure and the oily mass was purified by reverse phase chromatography (water/acetonitrile) and lyophilized to give 1.6 g of the title compound as a white solid: $^1$H NMR (d$_6$-DMSO) δ1.15 (t, 3H, J=7.5 Hz), 1.48 (m, 2H), 1.56 (m, 2H), 1.75 (m, 2H), 2.10 (m, 2H), 2.41 (m, 2H), 2.68 (m, 2H), 3.9 (m, 1H), 4.0 (q, 2H, J=7.5 Hz), 4.02 (m, 2H), 7.35 (m, 9H), 7.7 (bd, 1H, J=7.9 Hz), 9.05 (bs, 2H), 9.3 (bs, 2H)MS (FAB) m/e 474.1 (M+H+)

Elemental Analysis Required for $C_{24}H_{31}N_3O_4S.F_3$. $C_2O_2H$ C 52.20 H 5.46 N 6.39 Found C 52.41 H 5.30 N 6.88

EXAMPLE 17

Preparation of (±)-3-[[5-[4-(aminoiminomethyl)phenyl]-1-oxopentyl]amino]-5-(methylthio)pentanoic acid

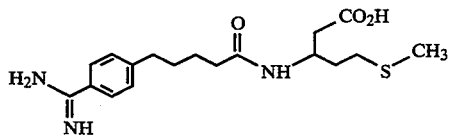

Step 1. Preparation of (±)-3-amino-5-(thiomethyl)pentanoic acid:

To acrolein (6 ml) in methylene chloride (125 ml) stirring, at 0° C. was added 1,8-diazabicyclo [5.4.0]undec-7-ene (DBU) (100 mg) and sodium thiomethoxide (15 g). After completion of the Michael addition as determined by TLC, (30% ethylacetate in hexanes)or utilizing commercially available 3-(methylthio)propionaldehyde, ethyl diazoacetate (10 ml) was added followed by tin(II)chloride (250 mg) and the reaction was left to stir until TLC showed a single product. The reaction mixture was diluted with methylene chloride (100 ml), washed with 50 ml 10% aq. HCl, dried over Na$_2$SO$_4$, and the solvent was removed under reduced pressure to give the β-ketoester. $^1$H NMR (d$_6$-DMSO) δ1.3 (t, 3H, J=7.8 Hz), 2.0 (s, 3H), 2.2 (m, 2H), 2.8 (m, 2H), 3.4 (s, 2H), 4.1 (s, 2H), 4.2 (q, 2H, J=7.8 Hz).

The crude β-keto ester (10 g, 57 mmol) was dissolved in methanol (200 ml) and ammonium formate (36 g, 570 mmol) and NaCNBH$_3$ (3.7 g, 57 mmol) were added. The reaction mixture was stirred at room temperature for 24 hours and the solvent was removed under reduced pressure to afford a white mass which was taken up in methylene chloride (200 ml) and filtered. The solvent was removed under reduced pressure to afford an oil which was dissolved in 1N HCl (200 ml) and extracted with ether (100 ml). The ether layer was discarded and the aqueous layer was adjusted to pH 10 with 50% aqueous sodium hydroxide solution. The product was purified by reverse phase chromatography (water/acetonitrile) and lyophilized to provide 3.5 g of a white solid [3-amino-5-(methylsulfide)pentanoic acid]; $^1$H NMR (d$_6$-DMSO) δ1.96 (m, 2H), 2.55 (m, 2H), 2.69 (m, 2H), 3.52 (m, 1H), 3.75 (s, 2H), 7.4(m, 5H), 8.3 (bs, 2H); MS (FAB) m/e 164.2 (M+H+).

Step 2. Coupling of 5-(p-benzamidine)pentanoic acid (BAP) with (±)-3-amino-5-(thiomethyl)pentanoic acid from step 1.

5-(p-Benzamidine)pentanoic acid (1.5 g) was added to dry DMF (100 ml) under a nitrogen atmosphere and N,N$^1$-disuccinimidyl carbonate (1.5 g) and DMAP (100 mg) were added. After the reaction became homogeneous the β-amino acid from step 1 (2 g) in aqueous 10 ml 5% K$_2$CO$_3$ was added. After 1 hour the solvent was removed under reduced pressure, the oily mass was dissolved in water, purified by reverse phase chromatography (water/acetonitrile) and lyophilized to give 1.6 g of the title compound as a white solid: $^1$H NMR (d$_6$-DMSO) δ1.51 (m, 4H), 1.56 (m, 2H), 2.0 (s, 3H), 2.08 (m, 2H), 2.90 (m, 4H), 2.71 (m, 2H), 4.10 (m, 1H), 7.35 (m, 9H), 7.7 (bd, 1H, J=7.9 Hz), 9.10 (bs, 2H), 9.25 (bs, 2H); MS (FAB) m/e 366.2 (M+H+).

Elemental Analysis Required for $C_{18}H_{27}N_3O_4S.F_3$. $C_2O_2H$ C 49.17 H 5.98 N 8.60 Found C 49.47 H 5.85 N 8.59

EXAMPLE 18

Preparation of (±)-3-[[5-[4-(aminoiminomethyl)phenyl]-1-oxopentyl]amino]-5-(methylsulfinyl)pentanoic acid

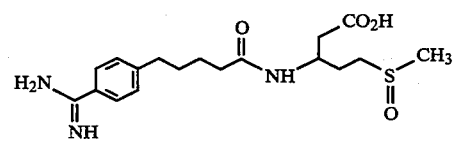

(±)-3-[[5-[4-(Aminoiminomethyl)phenyl]-1-oxopentyl]amino]-5-(methylthio)pentanoic acid (2.5 g) was added to water (15 ml) and acetic acid (5 ml) and 30% H$_2$O$_2$ (10 ml). The oxidation was allowed to proceed for 14 hours after which the reaction mixture was purified by reverse phase chromatography (water/acetonitrile) and lyophilized to give 1.6 g of the title compound as a white solid: $^1$H NMR (d$_6$-DMSO) δ1.51 (m, 4H), 1.56 (m, 2H), 2.0(m, 2H), 2.18 (s, 3H), 2.90 (m, 4H), 2.71 (m, 2H), 4.10 (m, 1H), 7.35 (m, 9H), 7.7 (bd, 1H, J=7.9 Hz), 9.10 (bs, 2H), 9.25 (bs, 2H); MS (FAB) m/e 382 2 (M+H+).

Elemental Analysis Required for $C_{18}H_{27}N_3O_4S.F_3$. $C_2O_2H$ C 44.92 H 5.29 N 7.48 Found C 44.99 H 5.44 N 7.33

EXAMPLE 19

Preparation of (±)-3-[[5-[4-(aminoiminomethyl)phenyl]-1-oxopentyl]amino]-5-(methylsulfonyl)pentanoic acid

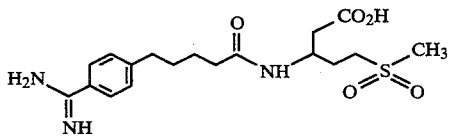

(±)-3-[[5-[4-(Aminoiminomethyl)phenyl]-1oxopentyl]amino]-5-(methylthio)pentanoic acid (2.5 g) was added to water (15 ml) and acetic acid (5 ml) and 30% $H_2O_2$ (10 ml). The oxidation was allowed to proceed for 48 hours after which the reaction mixture was purified by reverse phase chromatography (water/acetonitrile) and lyophilized to give 1.6 g of the title compound as a white solid: $^1$H NMR (d$_6$-DMSO) δ1.51 (m, 4H), 1.56 (m, 2H), 2.0 (m, 2H), 2.10 (s, 3H), 2.90 (m, 4H), 2.71 (m, 2H), 4.10 (m, 1H), 7.35 (m, 9H), 7.7 (bd, 1H, J=7.9 Hz), 9.10 (bs, 2H), 9.25 (bs, 2H); MS (FAB) m/e 398.2 (M+H+).

Elemental Analysis Required for $C_{18}H_{27}N_3O_5S.F_3.C_2O_2H$ C 44.37 H 5.05 N 7.39 Found C 44.29 H 5.21 N 7.42

EXAMPLE 20

Preparation of 4-(aminoiminomethyl)-N-[2-[(4-methylphenyl)sulfinyl]ethylbenzenepentanamide

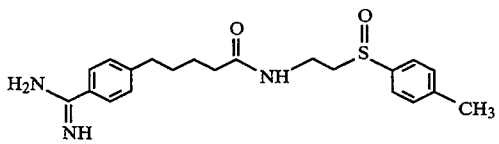

Step 1.
To 150 ml DMF and water (10:1) p-tolylthiophenol (10 g, 80.6 mmol) was added, followed by K$_2$CO$_3$ (12 g, 81 mmol), bromoacetonitrile (9.67 g, 80.6 mmol), tetraethyl ammonium hydrogen sulfate (200 mg), sodium iodide (200 mg) and stirred at 25° C. for 24 hours. After this time the mixture was diluted with water and extracted with diethyl ether. The ether extracts were washed with water and dried over MgSO$_4$. The crude nitrile was added to THF (60 ml) followed by 100 ml borane/THF (1N). The solution was refluxed for 16 hours. The solution was cooled in an ice bath and 100 ml of 10% acetic acid in methanol was added to remove excess borane. The solution was concentrated under reduced pressure then treated with 200 ml diethyl ether and washed with 50 ml sat. K$_2$CO$_3$ and dried over Na$_2$SO$_4$ to leave the amino-2-(4-tolylsulfide)ethane.
Step 2. Coupling of 5-(p-benzamidine)pentanoic acid (BAP) with amino-2-(4-tolylsulfide)ethane of step 1.

5-(p-Benzamidine)pentanoic acid (1.5 g) was added to dry DMF (100 ml) under a nitrogen atmosphere and N,N$^1$-disuccinimidyl carbonate (1.5 g) and DMAP (100 mg) at 25° C. were added. After the reaction became homogeneous, amino-2-(-4-tolylsulfide)ethane from step 1 (2 g) in 10 ml 5% aq. K$_2$CO$_3$ was added. After 1 hour the solvent was removed under reduced pressure and the oily mass was dissolved in water (15 mL) followed by the addition of 30% H$_2$O$_2$ (5 mL) and glacial acetic acid (5 ml). The oxidation was allowed to proceed for 4 hours after which the reaction mixture was purified by reverse phase chromatography (water/acetonitrile) and lyophilized to give 1.6 g of the title compound as a white solid: $^1$H NMR (d$_6$-DMSO) δ1.51 (m, 4H), 2.1 (m, 2H), 2.08 (m, 2H), 2.38 (s, 3H), 2.67 (m, 2H), 2.71 (m, 2H), 2.85 (m, 1H), 2.9 (m, 1H), 3.22 (m, 1H), 3.35 (m, 1H), 7.35 (m, 9H), 7.7 (m, 1H), 9.10 (bs, 2H), 9.20(bs, 2H); MS (FAB) m/e 386.2 (M+H+).

Elemental Analysis Required for $C_{21}H_{27}N_3O_2S.F_3.C_2O_2H$ C 53.60 H 5.43 N 8.20 Found C 53.61 H 5.53 N 8.06

EXAMPLE 21

Preparation of 4-(aminoiminomethyl)-N-[2-[(4methylphenyl)sulfonyl]ethylbenzenepentanamide

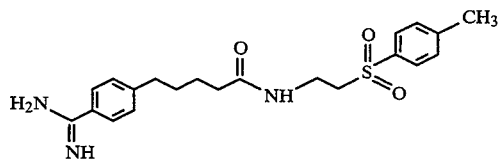

4-(Aminoiminomethyl)-N-[2-[(4-methylphenyl)sulfinyl]ethylbenzenepentanamide (2.5 g) was added to water (15 ml), acetic acid (5 ml) and 30% H$_2$O$_2$ (10 ml). The oxidation was allowed to proceed for 48 hours after which the reaction mixture was purified by reverse phase chromatography (water/acetonitrile) and lyophilized to give 1.6 g of the title compound as a white solid: $^1$H NMR (d$_6$-DMSO) δ1.51 (m, 4H), 2.1 (m, 2H), 2.08 (m, 2H), 2.38 (s, 3H), 2.67 (m, 2H), 2.71 (m, 2H), 3.28 (m, 2H), 3.35 (m, 2H), 7.35 (m, 9H), 7.7 (m, 1H), 9.10 (bs, 2H), 9.20 (bs, 2H); MS (FAB) m/e 402.5 (M+H+).

Elemental Analysis Required for $C_{21}H_{27}N_3O_3S.F_3.C_2O_2H$ C 52.70 H 5.34 N 8.01 Found C 52.88 H 5.45 N 7.94

EXAMPLE 22

Preparation of (±)-β-[[5-[4-(aminoiminomethyl)phenyl]-1-oxopentyl]amino]-2-(methylsulfinyl)benzenepropanoic acid

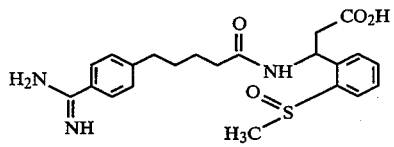

Step 1. Preparation of (±)-3-amino-3-(2methylthiophenyl)propanoic acid.

Ethyl hydrogen malonate (13.7 g, 104 mmol) was added to 2-methylthiobenzaldehyde (10 g, 104 mmol) and ammonium acetate (20 g, 260 mmol) in dry ethanol. The solution was heated to reflux for 6 hours. After this time the solvent was removed under reduced pressure to leave an oil. To this oil 10% HCl (250 ml) was added along with ether (100 ml). The ether layer was discarded and the aqueous layer was made basic with K$_2$CO$_3$, then extracted twice with methylene chloride (100 ml), dried over Na$_2$SO$_4$ and solvent removed to give 6 g of a yellow oil which was purified by reverse phase chromatography (water/acetonitrile) and lyophilized to give 4.6 g of a white solid: $^1$H NMR (300 MHz)

(d6-DMSO) δ2.5 (s, 3H), 2.91 (m, 2H), 5.15 (m, 1H), 7.54 (m, 4H); MS (FAB) m/e (M+H+): 212.0.

Step 2. Coupling of 5-(p-benzamidine)pentanoic acid (BAP) with amino-3-(2-methylthiophenyl)propionic acid in step 1.

5-(p-Benzamidine)pentanoic acid (1.5 g) was added to dry DMF (100 ml) under a nitrogen atmosphere and N,N¹-disuccinimidyl carbonate (1.5 g) and DMAP (100 mg) were added at 25° C. After the reaction became homogeneous amino-3-(2-methylthiophenyl)propionic acid from step 1 (2 g) in 10 ml 5% aq. $K_2CO_3$ was added. After 1 hour the solvent was removed under reduced pressure and the oily mass was dissolved in water (15 mL) followed by the addition of 30% $H_2O_2$ (5 mL) and glacial acetic acid (5 ml). The oxidation was allowed to proceed for 4 hours after which the reaction mixture was purified by reverse phase chromatography (water/acetonitrile) and lyophilized to give 1.6 g of the title compound as a white solid: ¹H NMR (d6-DMSO) δ1.42 (m, 4H), 2.01 (m, 2H), 2.63 (m, 4H), 2.76 (s, 3H), 5.22 (m, 1H), 7.35 (m, 9H), 7.7 (m, 1H), 9.10 (bs, 2H), 9.20 (bs, 2H); MS (FAB) m/e 430.2 (M+H+).

Elemental Analysis Required for $C_{22}H_{27}N_3O_4S.F_3$-$C_2O_2H$ C 50.71 H 5.52 N 7.25 Found C 50.33 H 5.88 N 7.11

EXAMPLE 23

Preparation of (±)-β-[[5-[4-(aminoiminomethyl)phenyl]-1-oxopentyl]amino]-2-(methylsulfonyl)benzenepropanoic acid

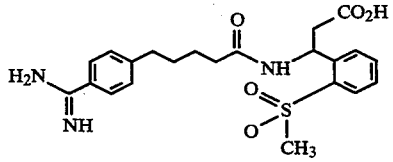

(±)-β-[[5-[4-(Aminoiminomethyl)phenyl]-1-oxopentyl]amino]-2-(methylsulfinyl)benzenepropanoic acid (2.5 g) was added to water (15 ml), acetic acid (5 ml) and followed by the addition of 30% $H_2O_2$ (10 mL). The oxidation was allowed to proceed for 48 hours after which the reaction mixture was purified by reverse phase chromatography (water/acetonitrile) and lyophilized to give 1.6 g of the title compound as a white solid: ¹H NMR (d6-DMSO) δ1.52 (m, 4H), 2.01 (m, 2H), 2.63 (m, 4H), 3.50 (s, 3H), 5.82 (m, 1H), 7.35 (m, 9H), 7.7 (m, 1H), 9.10 (bs, 2H), 9.20 (bs, 2H); MS (FAB) m/e 446.2 (M+H+).

Elemental Analysis Required for $C_{22}H_{27}N_3O_5S.F_3$-$C_2O_2H$ C 40.97 H 4.64 N 5.97 Found C 40.80 H 4.34 N 5.81

EXAMPLE 24

Preparation of ethyl 3S-[[5-[4-(aminoiminomethyl)phenyl]-1-oxopentyl]amino]-4-(2-pyridinylsulfonyl)butanoate

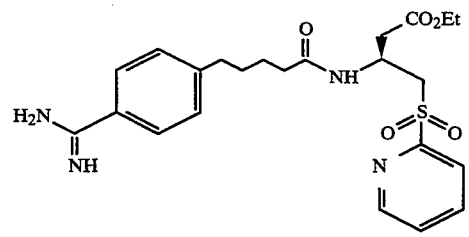

Step 1. Preparation of benzyl-3-N-tBoc-amino-4-hydroxy-(3S)-butyrate

N-tBoc-L-aspartic acid, β-benzyl ester (75 g, 232 mmol) was dissolved in 100 ml of THF and added dropwise over a period of 30 min to 400 ml of 1N $BH_3$. THF at 0° C. under a $N_2$ atmosphere. After the solution was stirred for 2.5 hours at 0° C., the reaction was quenched with a 50 ml solution of 10% acetic acid in methanol, and the solvent was evaporated under reduced pressure. The residue was dissolved in ether (200 ml) and washed with 50 ml 1N HCl, 50 ml sat. $K_2CO_3$, 50 ml water and dried over $MgSO_4$. The product was isolated by removal of the solvent under reduced pressure (mp 56°-57° C. from isopropyl ether/hexane). ¹H NMR (d6-DMSO) δ1.4 (s, 9H), 2.68 (d, 2H, J=6 Hz), 3.82 (d, 2H, J=5 Hz), 4.01 (m, 1H), 5.16 (s, 2H), 5.2 (bs, 1H), 7.37 (bs, 5H).

Step 2. Preparation of (3S)-Benzyl-3-amino-4-(2-pyridylsulfone)butyrate

Benzyl-3-N-tBoc-amino-4-hydroxy-(3S)-butyrate (20 g, 64.7 mmol) was dissolved in 200 ml of methylene chloride followed by triethylamine (9.8 g, 97 mmol) and cooled to 0° C. Methanesulfonyl chloride (9.6 g, 84 mmol) was added and the solution was stirred for 2-3 hours. After this time more methylene chloride (100 ml) was added and the solution was washed with 100 ml water, and dried over $MgSO_4$ to give 27 g of the mesylate after removal of the solvent. ¹H NMR (d6-DMSO) δ1.45 (s, 9H), 2.71 (d, 2H, J=6 Hz), 2.95 (s, 3H), 4.37 (bs, H), 4.7 (bs, 2H), 5.15 (s, 2H), 7.37 (bs, 5H).

The mesylate (27 g, 64 mmol) from step 2 was added to 100 ml dry DMF followed by 2-mercaptopyridine, 18-crown-6, catalytic DMAP and stired at 25° C. for 24 hours. After the reaction was completed, 100 ml water was added and the product was extracted with ether (2×150 ml). The ether extracts were washed with (2×75 ml) water, dried over $MgSO_4$, and the solvent evaporated to give benzyl-3-N-tBoc-amino-4-(2-pyridylsulfide)-(3S)-butyrate (22 g).

The crude benzyl-3-N-tBoc-amino-4-(2-pyridylsulfide)-(3S)-butyrate was dissolved in dioxane (100 ml) and 4N HCl in dioxane (10 ml) was added. After 6 hours the dioxane was removed under reduced pressure to leave an oil which was dissolved in water (200 ml) and washed with ether (100 ml). The ether layer was discarded and the aqueous layer was made basic (pH 10)using solid $K_2CO_3$. The product was extracted into methylene chloride (2×100 ml), dried over $Na_2SO_4$ and evaporated to give benzyl-3-amino-4-(2-pyridylsulfide)-(3S)-butyrate (8 g). ¹H NMR (d6-DMSO) δ1.6 (bs, 2H), 2.5-2.7 (m, 4H), 3.5 (m, 1H), 5.16 (s, 2H), 7.36 (bs, 5H);

H), 4.05 (m, 3H), 7.8 (s, 4H); MS (FAB) m/e 219.0 (M+H+).

Step 3. Coupling of 5-(p-benzamidine)pentanoic acid (BAP) with (3S)-benzylamino-3-(2-mercaptopyridyl)-propionic acid in step 1.

5-(p-Benzamidine)pentanoic acid (1.5 g) was added to dry DMF (100 ml) under a nitrogen atmopshere and N,N$^1$-disuccinimidyl carbonate (1.5 g) and DMAP (100 mg) at 25° C. were added. After the reaction mixture became homogeneous, (3S)-benzylamino-3-(2mercaptopyridyl)propionic acid from step 1 (2 g) in 10 ml 5% aq. $K_2CO_3$ was added. After 1 hour the solvent was removed under reduced pressure and the oily mass was dissolved in water (15 ml) followed by the addition of 30% $H_2O_2$ (5 ml) and glacial acetic acid (5 ml). The oxidation was allowed to proceed for 24 hours. The solvent was removed under reduced pressure, ethanol (50 ml) was added and the reaction mixture was allowed to stir for 48 hours. The solvent was removed under reduced pressure and the product was purified by reverse phase chromatography (water/acetonitrile) and lyophilized to give 1.6 g of the title compound of a white solid: $^1$H NMR (d$_6$-DMSO) δ1.2 (t, 3H, J=8.0 Hz), 1.40 (m, 2H), 1.49 (m, 2H), 1.8 (m, 2H), 2.63 (m, 4H), 3.76 (m, 2H), 4.0 (q,2H, J=8.0 Hz), 4.44 (m, 1H), 7.35 (m, 8H), 7.7 (m, 1H), 9.10 (bs, 2H), 9.20 (bs, 2H); MS (FAB) m/e 475.2 (M+H+).

Elemental Analysis Required for $C_{23}H_{30}N_4O_5S.F_3$-$C_2O_2H$ C 50.25 H 5.36 N 9.38 Found C 50.01 H 5.17 N 9.32

EXAMPLE 25

Preparation of $^1$-methylethyl 3S-[[5-[4-(aminoiminomethyl)phenyl]-1-oxopentyl-]amino]-4-(2pyridinylsulfonyl)butanoate

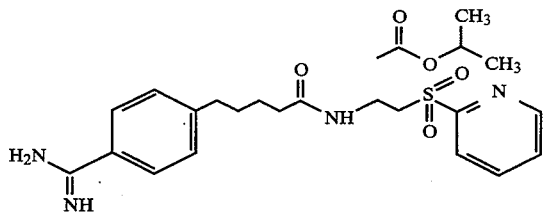

Ethyl 3S-[[5-[4-(aminoiminomethyl)phenyl]-1oxopentyl]amino]-4 -(2 -pyridinylsulfonyl)butanoate (2.5 g) was added to isopropanol (50 ml) followed by 4N hydrochloric acid in dioxane (10 ml). This solution was allowed to stir for 48 hours after which the solvent was removed under reduced pressure and the product was purified by reverse phase chromatography (water/acetonitrile) and lyophilized to give 1.6 g of a white solid: $^1$H NMR (d$_6$-DMSO) δ1.2 (d, 6H, J=7.8 Hz), 1.40 (m, 2H), 1.49 (m, 2H), 1.8 (m, 2H), 2.63 (m, 4H), 3.76 (m, 2H), 4.0 (q, 2H, J=8.0 Hz), 4.44 (m, 1H), 4.8 (m, 1H), 7.35 (m, 8H), 7.7 (m, 1H), 9.10 (bs, 2H), 9.20 (bs, 2H); MS (FAB) m/e 489.3 (M+H+).

Elemental Analysis Required for $C_{24}H_{32}N_4O_5S.F_3$-$C_2O_2H$ C 50.35 H 5.63 N 9.00 Found C 50.36 H 5.31 N 8.94

EXAMPLE 26

Compounds of the invention were evaluated by an in vitro assay to determine compound activity as an inhibitors of platelet aggregation.

In-Vitro Platelet Aggregation in PRP

Healthy male or female dogs were fasted for 8 hours prior to drawing blood; then 30 ml whole blood from jugular vein was collected using a butterfly needle and 30 ml plastic syringe with 3 ml of 0.129M buffered sodium citrate (3.8%). The syringe was rotated carefully as blood was drawn to mix the citrate. The whole blood was transferred to a 50 ml Corning Conical sterile centrifuge tube. Platelet-rich plasma (PRP) was prepared by centrifugation at 975×g for 3.17 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP platelet count was typically a count of 2.5–4×$10^8$ platelets per ml. 400 μL of the PRP preparation and 50 μL of the compound to be tested or saline were preincubated for 2 minutes at 37° C. in a BioData aggregometer (BioData, Horsham, PA). 50 μL of Collagen (equine tendon, Chronolog, Havertown, Pa.) [33.3 μg/m, final concentration] was added to the cuvettes and the aggregation was monitored for 4 minutes. All compounds are tested in duplicate. Inhibition of aggregation for each sample was determined using the formula: % of inhibition=100- % of control and % of control=(T$_{inh}$—T$_{bas}$)/(T$_{agg}$—T$_{bas}$)×100, where T$_{bas}$ is % of light transmission in PRP (baseline), T$_{agg}$ is % of light transmission in the aggregated PRP sample (saline control) and T$_{inh}$ is % of light transmission in the sample containing the inhibitor.

The compounds tested, the inhibition observed at a test concentration of 10 μM, and the concentrations at which the test compounds inhibit aggregation by 50% (IC$_{50}$)are recorded in Table 1.

TABLE I

| IN-VITRO PLATELET AGGREGATION IN PRP | | | |
|---|---|---|---|
| Compound | % Inhibition | Test Concentration | Dog PRP IC$_{50}$ Micro M |
| (±)-3-[[5-[4-(aminoiminomethyl)phenyl]-1-oxopentyl]amino]-5-[(phenylmethyl)sulfonyl]pentanoic acid | 100 | 1 × 10$^{-5}$ | .220 |
| (±)-3-[[5-[4-(aminoiminomethyl)phenyl]-1-oxopentyl]amino]-4-[(4-methylphenyl)sulfonyl]butanoic acid | 100 | 1 × 10$^{-5}$ | .130 |
|  | 100 | 1 × 10$^{-5}$ | .0400 |
| (±)-3-[[5-[4-(aminoiminomethyl)phenyl]-1-oxopentyl]amino]-4-(2-pyridinylsulfonyl)butanoic acid | 100 | 1 × 10$^{-5}$ | .032 |
|  | 100 | 1 × 10$^{-5}$ | .075 |
| (±)-ethyl 3-[[5-[4-(aminoiminomethyl)phenyl]-1-oxopentyl]amino]-4-[4-methylphenyl)sulfonyl]butanoate | 22 | 1 × 10$^{-5}$ | N/D |
|  | 7 | 1 × 10$^{-5}$ |  |
| (±)-3-[[5-[4-(aminoiminomethyl)phenyl]-1-oxopentyl]amino]-4-(phenylsulfonyl)butanoic acid | 100 | 1 × 10$^{-5}$ | .028 |
| (±)ethyl 3-[[5-[4-(aminoiminomethyl) phenyl]-1-oxopentyl]amino]-4-phenylsulfonyl)butanoate | 3 | 1 × 10$^{-5}$ | N/D |

TABLE I-continued
IN-VITRO PLATELET AGGREGATION IN PRP

| Compound | % Inhibition | Test Concentration | Dog PRP IC$_{50}$ Micro M |
|---|---|---|---|
| ($\pm$)-3-[[5-[4-(aminoiminomethyl)phenyl]-1-oxopentyl]amino]-5-(methylsulfonyl)pentanoic acid | 100 | $1 \times 10^{-5}$ | .700 |
| ($\pm$)-3-[[5-[4-(aminoiminomethyl)phenyl]-1-oxopentyl]amino]-4-[(4-methoxyphenyl)sulfonyl]butanoic acid | 100 | $1 \times 10^{-5}$ | .130 |
| ($\pm$)-ethyl 3-[[5-[4-(aminoiminomethyl)phenyl]-1-oxopentyl]amino]-4-(2-pyridinylsulfonyl)butanoate | NT | NT | NT |
| ($\pm$)-3-[[5-[4-(aminoiminomethyl)phenyl]-1-oxopentyl]amino]-4-(4-fluorophenyl)sulfonyl]butanoic acid | 100 | $1 \times 10^{-5}$ | .120 |
| 4-(aminoiminomethyl)-N-[2-[4-methylphenyl)sulfonyl]ethylbenzenepentanamide | 23 | $1 \times 10^{-5}$ | N/D |
| ($\pm$)-3-[[5-[4-(aminoiminomethyl)phenyl]-1-oxopentyl]amino]-4-[(phenylsulfinyl]butanoic acid | 100 | $1 \times 10^{-5}$ | .200 |
| ($\pm$)-ethyl 3-[[5-[4-(aminoiminomethyl)phenyl]-1-oxopentyl]amino]-4-(4-phenylsulfinyl)butanoate | 0 | $1 \times 10^{-5}$ | N/D |
| ($\pm$)-3-[[5-[4-(aminoiminomethyl)phenyl]-1-oxopentyl]amino]-5-(methylsulfinyl)pentanoic acid | 100 | $1 \times 10^{-5}$ | 1.5 |
| 4-(aminoiminomethyl)-N-[2-[(4-methylphenyl)sulfinyl]ethylbenzenepentanamide | 0 | $1 \times 10^{-5}$ | N/D |
| ($\pm$)-3-[[5-[4-(aminoiminomethyl)phenyl]-1-oxopentyl]amino]-5-(methylthio)pentanoic acid | 100 | $1 \times 10^{-5}$ | 1.3 |
| ($\pm$)-3-[[5-[4-(aminoiminomethyl)phenyl]-1-oxopentyl]amino]-4-[(4-fluorophenyl)thio]butanoic acid | 100 | $1 \times 10^{-5}$ | 1.80 |
| ($\pm$)-3-[[5-[4-(aminoiminomethyl)phenyl]-1-oxopentyl]amino]-4-(phenylthio)butanoic acid | 100 | $1 \times 10^{-5}$ | .500 |
| ($\pm$)-ethyl 3-[[5-[4-(aminoiminomethyl)phenyl]-1-oxopentyl]amino]-4-[(4-phenylthio]butanoate | 0 | $1 \times 10^{-5}$ | N/D |
| ethyl 3S-[[5-[4-(aminoiminomethyl)phenyl]-1-oxopentyl]amino]-4-(2-pyridinylsulfonyl)butanoate | NT | NT | NT |
| 1-methylethyl 3S-[[5-[4-(aminoiminomethyl)phenyl]-1-oxopentyl]amino]-4-(2-pyridinylsulfonyl)butanoate | 28 | $1 \times 10^{-5}$ | N/D |
| ($\pm$)-ethyl 3-[[5-[4-(aminoiminomethyl)phenyl]-1-oxopentyl]amino]-5-[(phenylmethyl)sulfinyl]pentanoate | 100 | $1 \times 10^{-5}$ | .420 |
| ($\pm$)-3-[[5-[4-(aminoiminomethyl)phenyl]-1-oxopentyl]amino]-5-(phenylmethyl)sulfinyl]pentanoic acid | 100 | $1 \times 10^{-5}$ | .100 |

N/D = not determined
NT = not tested

What we claim is:

1. A compound of the formula

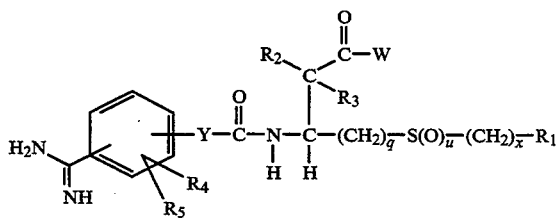

or a pharmaceutically acceptable salt thereof, wherein
$R_1$ is alkyl having 1 to 6 carbon atoms; phenyl; substituted phenyl wherein each substituent can be selected from the group consisting of alkyl having 1 to 6 carbon atoms, halo, alkoxy having 1 to 6 carbon atoms, carboxyl, trifluoromethyl, hydroxy and nitro; or pyridyl;
$R_2$ and $R_3$ are each independently hydrido or alkyl having 1 to 6 carbon atoms;
$R_4$ and $R_5$ are each independently hydrido, alkyl having 1 to 6 carbon atoms, alkoxy having 1 to 6 carbon atoms or halo;
Y is alkyl having 1 to 6 carbon atoms, alkenyl having 2 to 4 carbon atoms or alkynyl having 2 to 4 carbon atoms;
W is OR wherein R is hydrido or alkyl having 1 to 6 carbon atoms;
q is an integer from 1 to 4;
u is 0, 1, or 2; and
x is an integer from 0 to 3.

2. A compound of the formula

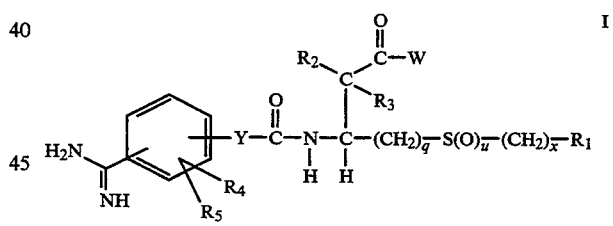

or a pharmaceutically acceptable salt thereof, wherein
$R_1$ is alkyl having 1 to 6 carbon atoms; phenyl; substituted phenyl wherein each substituent can be selected from the group consisting of alkyl having 1 to 6 carbon atoms, halo, alkoxy having 1 to 6 carbon atoms, carboxyl, trifluoromethyl, hydroxy and nitro; or pyridyl;
$R_2$ and $R_3$ are each independently hydrido or alkyl having 1 to 6 carbon atoms;
$R_4$ and $R_5$ are each independently hydrido, alkyl having 1 to 6 carbon atoms, alkoxy having 1 to 6 carbon atoms or halo;
Y is alkyl having 1 to 6 carbon atoms, alkenyl having 2 to 4 carbon atoms or alkynyl having 2 to 4 carbon atoms;
W is OR wherein R is hydrido or alkyl having 1 to 6 carbon atoms;
q is an integer from 1 to 4;
u is 2; and
x is an integer from 0 to 3.

3. A compound according to claim 2 wherein $R_1$ is phenyl; substituted phenyl wherein each substituent can be selected from the group consisting of alkyl having 1 to 6 carbon atoms, halo, alkoxy having 1 to 6 carbon atoms, carboxyl; or pyridyl.

4. A compound according to claim 3 wherein the compound is (±)-3-[[5-[4-(aminoiminomethyl)phenyl]-1-oxopentyl]amino]-5-[(phenylmethyl)sulfonyl]pentanoic acid.

5. A compound according to claim 3 wherein the compound is (±)-3-[[5-[4-(aminoiminomethyl)phenyl]-1-oxopentyl]amino]-4-[(4-methylphenyl)sulfonyl]butanoic acid.

6. A compound according to claim 3 wherein the compound is (±)-3-[[5-[4-(aminoiminomethyl)phenyl]-1-oxopentyl]amino]-4-(2-pyridinylsulfonyl)butanoic acid.

7. A compound according to claim 3 wherein the compound is (±)-ethyl 3-[[5-[4-(aminoiminomethyl)phenyl]-1-oxopentyl]amino]-4-[(4-methylphenyl)sulfonyl]butanoate.

8. A compound according to claim 3 wherein the compound is (±)-3-[[5-[4-(aminoiminomethyl)phenyl]-1-oxopentyl]amino]-4-(phenylsulfonyl)butanoate.

9. A compound according to claim 3 wherein the compound is (±)-ethyl 3-[[5-[4-(aminoiminomethyl)phenyl]-1-oxopentyl]amino]-4-(phenylsulfonyl)butanoate.

10. A compound according to claim 3 wherein the compound is (±)-3-[[5-[4-(aminoiminomethyl)phenyl]-1-oxopentyl]amino]-5-(methylsulfonyl)pentanoic acid.

11. A compound according to claim 3 wherein the compound is (±)-3-[[5-[4-(aminoiminomethyl)phenyl]-1-oxopentyl]amino]-4-[(4-methoxyphenyl)sulfonyl]butanoic acid.

12. A compound according to claim 3 wherein the compound is (±)-ethyl 3-[[5-[4-(aminoiminomethyl)phenyl]-1-oxopentyl]amino]-4-(2-pyridinylsulfonyl)butanoate.

13. A compound according to claim 3 wherein the compound is (±)-3-[[5-[4-(aminoiminomethyl)phenyl]-1-oxopentyl]amino]-4-[(4-fluorophenyl)sulfonyl]butanoic acid.

14. A compound according to claim 3 wherein the compound is 4-(aminoiminomethyl)-N-[2-[(4-methylphenyl)sulfonyl]ethylbenzenepentanamide.

15. A compound according to claim 3 wherein the compound is (±)-3-[[5-[4-(aminoiminomethyl)phenyl]-1-oxopentyl]amino]-4-[(4-methoxyphenyl)sulfonyl]butanoic acid.

16. A compound according to claim 3 wherein the compound is ethyl 3S-[[5-[4-(aminoiminomethyl)phenyl]-1-oxopentyl]amino]-4-(2-pyridinylsulfonyl)butanoate.

17. A compound according to claim 3 wherein the compound is 1-methylethyl 3S-[[5-[4-(aminoiminomethyl)phenyl]-1-oxopentyl]amino]-4-(2-pyridinylsulfonyl)butanoate.

18. A compound according to claim 1 of the formula is

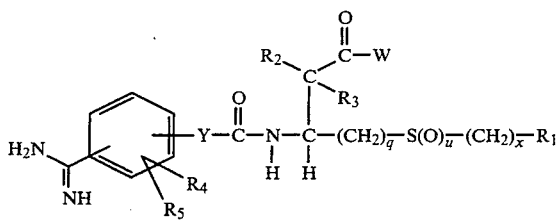

or a pharmaceutically acceptable salt thereof, wherein
$R_1$ is alkyl having 1 to 6 carbon atoms; phenyl; substituted phenyl wherein each substituent can be selected from the group consisting of alkyl having 1 to 6 carbon atoms, halo, alkoxy having 1 to 6 carbon atoms, carboxyl, trifluoromethyl, hydroxy and nitro;
$R_2$ and $R_3$ are each independently hydrido or alkyl having 1 to 6 carbon atoms;
$R_4$ and $R_5$ are each independently hydrido, alkyl having 1 to 6 carbon atoms, alkoxy having 1 to 6 carbon atoms or halo;
Y is alkyl having 1 to 6 carbon atoms, alkenyl having 2 to 4 carbon atoms or alkynyl having 2 to 4 carbon atoms;
W is OR wherein R is hydrido or alkyl having 1 to 6 carbon atoms;
q is an integer from 1 to 4;
u is 1; and
x is an integer from 0 to 3.

19. A compound according to claim 18 wherein the compound is (±)-3-[[5-[4-(aminoiminomethyl)phenyl]-1-oxopentyl]amino]-4-[phenylsulfinyl]butanoic acid.

20. A compound according to claim 18 wherein the compound is (±)-ethyl 3-[[5-[4-(aminoiminomethyl)phenyl]-1-oxopentyl]amino]-4-[4-phenylsulfinyl]butanoate.

21. A compound according to claim 18 wherein the compound is (±)-3-[[5-[4-(aminoiminomethyl)phenyl]-1-oxopentyl]amino]-5-(methylsulfinyl)pentanoic acid.

22. A compound according to claim 18 wherein the compound is 4-(aminoiminomethyl)-N-[2-[(4-methylphenyl)sulfinyl]ethylbenzenepentanamide.

23. A compound according to claim 18 wherein the compound is (±)-ethyl 3-[[5-[4-(aminoiminomethyl)phenyl]-1-oxopentyl]amino]-5-[(phenylmethyl)sulfinyl]pentanoate.

24. A compound according to claim 18 wherein the compound is (±)-3-[[5-[4-(aminoiminomethyl)phenyl]-1-oxopentyl]amino]-5-[(phenylmethyl)sulfinyl]pentanoic acid.

25. A compound according to claim 1 of the formula is

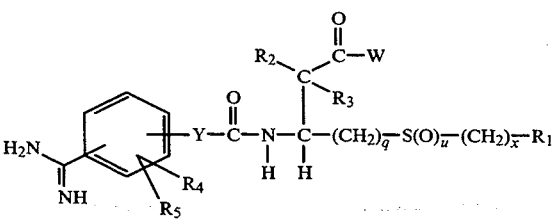

or a pharmaceutically acceptable salt thereof, wherein
$R_1$ is alkyl having 1 to 6 carbon atoms; phenyl; or substituted phenyl wherein each substituent can be selected from the group consisting of alkyl having 1 to 6 carbon atoms, halo, alkoxy having 1 to 6 carbon atoms, carboxyl, trifluoromethyl, hydroxy and nitro;

$R_2$ and $R_3$ are each independently hydrido or alkyl having 1 to 6 carbon atoms;

$R_4$ and $R_5$ are each independently hydrido, alkyl having 1 to 6 carbon atoms, alkoxy having 1 to 6 carbon atoms or halo;

Y is alkyl having 1 to 6 carbon atoms, alkenyl having 2 to 4 carbon atoms or alkynyl having 2 to 4 carbon atoms;

W is OR wherein R is hydrido or alkyl having 1 to 6 carbon atoms;

q is an integer from 1 to 4;
u is 0; and
x is an integer from 0 to 3.

26. A compound according to claim 25 wherein the compound is (±)-3-[[5-[4-(aminoiminomethyl)phenyl]-1-oxopentyl]amino]-5-(methylthio)pentanoic acid.

27. A compound according to claim 25 wherein the compound is (±)-3-[[5-[4-(aminoiminomethyl)phenyl]-1-oxopentyl]amino]-4-[(4-fluorophenyl)thio]butanoic acid.

28. A compound according to claim 25 wherein the compound is (±)-3-[[5-[4-(aminoiminomethyl)phenyl]-1-oxopentyl]amino]-4-(phenylthio)butanoic acid.

29. A compound according to claim 25 wherein the compound is (±)-ethyl 3-[[5-[4-(aminoiminomethyl)phenyl]-1-oxopentyl]amino]-4-(phenylthio)butanoate.

30. A pharmaceutical composition useful for inhibiting platelet aggregation comprising a therapeutically effective amount of a compound according to claim 1, together with one or more non-toxic pharmaceutically acceptable carriers.

31. A pharmaceutical composition according to claim 30 wherein the compound is selected from the group consisting of (±)-3-[[5-[4-(aminoiminomethyl)phenyl]-1-oxopentyl]amino]-4-(phenylsulfonyl)butanoic acid;

(±)-3-[[5-[4-(aminoiminomethyl)phenyl]-1-oxopentyl]amino]-5-(methylsulfonyl)pentanoic acid;

(±)-3-[[5-[4-(aminoiminomethyl)phenyl]-1-oxopentyl]amino]-4-[(4-fluorophenyl)thio]butanoic acid;

(±)-3-[[5-[4-(aminoiminomethyl)phenyl]-1-oxopentyl]amino]-4-[(4-methylphenyl)sulfonyl]butanoic acid;

(±)-3-[[5-[4-(aminoiminomethyl)phenyl]-1-oxopentyl]amino]-5-(methylthio)pentanoic acid;

(±)-3-[[5-[4-(aminoiminomethyl)phenyl]-1-oxopentyl]amino]-5-(methylsulfinyl)pentanoic acid;

(±)-3-[[5-[4-(aminoiminomethyl)phenyl]-1-oxopentyl]amino]-5-[(phenylmethyl)sulfonyl]pentanoic acid;

(±)-3-[[5-[4-(aminoiminomethyl)phenyl]-1-oxopentyl]amino]-4-[(4-fluorophenyl)sulfonyl]butanoic acid;

(±)-3-[[5-[4-(aminoiminomethyl)phenyl]-1-oxopentyl]amino]-5-(phenylmethyl)sulfinyl]pentanoic acid;

(±)-3-[[5-[4-(aminoiminomethyl)phenyl]-1-oxopentyl]amino]-4-(2-pyridinylsulfonyl)butanoic acid; and (±)-3-[[5-[4-(aminoiminomethyl)phenyl]-1-oxopentyl]amino]-4-(phenylsulfonyl)butanoic acid.

* * * * *

UNITED STATES PATENT AND TRADEMARK OFFICE
CERTIFICATE OF CORRECTION

PATENT NO. : 5,409,939
DATED : April 25, 1995
INVENTOR(S) : Adams, et al.

It is certified that error appears in the above-identified patent and that said Letters Patent is hereby corrected as shown below:

Column 3, line 1, that part of the formula reading

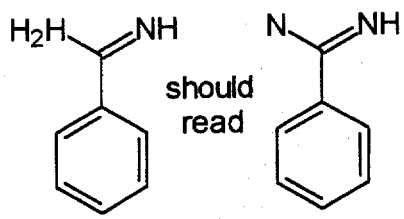

Column 7, line 20, column 24, line 14, column 35, line 13, and column 39, line 46, reading "1oxopentyl" should read --1-oxopentyl--.

Column 12, line 40, that part of the formula reading

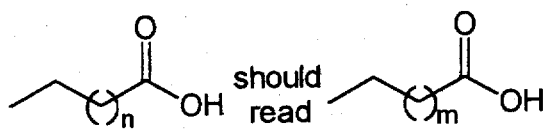

Column 12, line 67, reading "PPhhd3" should read --PPh$_3$--.

Column 36, line 54, reading "2methylthio" should read --2-methylthio--.

Column 39, line 33, reading "1methylethyl" should read --1-methylethyl--.

UNITED STATES PATENT AND TRADEMARK OFFICE
CERTIFICATE OF CORRECTION

PATENT NO. :    5,409,939

DATED      :    April 25, 1995

INVENTOR(S) :   Adams, et al.

It is certified that error appears in the above-identified patent and that said Letters Patent is hereby corrected as shown below:

Column 39, line 40, that part of the formula reading

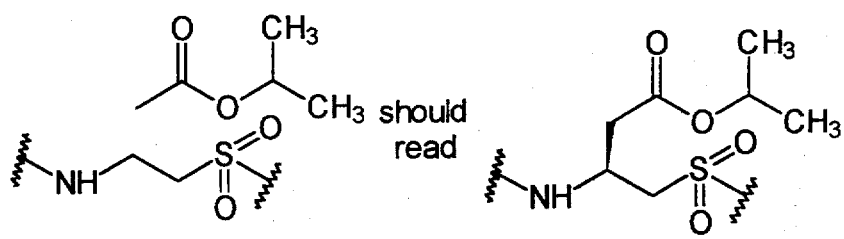

Column 39, line 65, column 41, line 13, reading "[4-methylphenyl" should read --[(4-methylphenyl--.

Signed and Sealed this

Fifteenth Day of July, 1997

Attest:

BRUCE LEHMAN

Attesting Officer        Commissioner of Patents and Trademarks